United States Patent
Bryant et al.

(10) Patent No.: US 11,844,764 B2
(45) Date of Patent: *Dec. 19, 2023

(54) AGITATION PROCESS FOR PREPARING A CARBETOCIN DRUG PRODUCT

(71) Applicant: ACADIA PHARMACEUTICALS, INC., San Diego, CA (US)

(72) Inventors: Christopher Bryant, Burr Ridge, IL (US); Mark C. Manning, Johnstown, CO (US); Ryan E. Holcomb, Fort Collins, CO (US)

(73) Assignee: ACADIA PHARMACEUTICALS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/684,742

(22) Filed: Mar. 2, 2022

(65) Prior Publication Data
US 2023/0014640 A1  Jan. 19, 2023

Related U.S. Application Data

(62) Division of application No. 17/529,861, filed on Nov. 18, 2021, now Pat. No. 11,298,399, which is a division of application No. 16/576,961, filed on Sep. 20, 2019, now Pat. No. 11,207,373.

(60) Provisional application No. 62/876,870, filed on Jul. 22, 2019, provisional application No. 62/734,134, filed on Sep. 20, 2018.

(51) Int. Cl.
| | | |
|---|---|---|
| *A61K 38/12* | (2006.01) | |
| *A61K 38/095* | (2019.01) | |
| *A61K 47/38* | (2006.01) | |
| *A61K 47/26* | (2006.01) | |
| *A61K 47/22* | (2006.01) | |
| *A61K 9/08* | (2006.01) | |

(52) U.S. Cl.
CPC ............ *A61K 38/095* (2019.01); *A61K 9/08* (2013.01); *A61K 47/22* (2013.01); *A61K 47/26* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 5,482,931 A | 1/1996 | Harris et al. | |
| 6,894,026 B1 | 5/2005 | Quay | |
| 7,879,976 B2 | 2/2011 | Friess | |
| 8,263,125 B2 | 9/2012 | Vaya et al. | |
| 8,853,158 B2 | 10/2014 | Muscatelli et al. | |
| 8,865,746 B2 | 10/2014 | Vath | |
| 9,016,221 B2 | 4/2015 | Brennan et al. | |
| 9,023,793 B2 | 5/2015 | Leonard et al. | |
| 9,125,862 B2 | 9/2015 | Muscatelli et al. | |
| 9,566,311 B2 | 2/2017 | Siekmann et al. | |
| 9,605,051 B2 | 3/2017 | Soane et al. | |
| 9,751,870 B2 | 9/2017 | Bissantz et al. | |
| 9,789,155 B2 | 10/2017 | Young et al. | |
| 9,867,881 B2 | 6/2018 | Soane et al. | |
| 10,016,513 B2 | 7/2018 | Soane et al. | |
| 2004/0235956 A1 | 11/2004 | Quay | |
| 2007/0032410 A1 | 2/2007 | Quay et al. | |
| 2010/0158995 A1 | 6/2010 | Millan et al. | |
| 2010/0292437 A1 | 11/2010 | Nelson et al. | |
| 2010/0311655 A1 | 12/2010 | Leonard et al. | |
| 2012/0108510 A1 | 5/2012 | Young et al. | |
| 2012/0172304 A1 | 7/2012 | Leonard et al. | |
| 2013/0102528 A1 | 4/2013 | Muscatelli et al. | |
| 2013/0116215 A1 | 5/2013 | Coma et al. | |
| 2013/0210746 A1 | 8/2013 | Siekmann et al. | |
| 2014/0329747 A1 | 11/2014 | Tidmarsh | |
| 2015/0165139 A1 | 6/2015 | Hafner | |

(Continued)

FOREIGN PATENT DOCUMENTS

| | | |
|---|---|---|
| CN | 102144965 A | 8/2011 |
| CN | 102977192 A | 3/2013 |

(Continued)

OTHER PUBLICATIONS

Avanti et al., "A new strategy to stabilize oxytocin in aqueous solutions: II. Suppression of cysteine-mediated intermolecular reactions by a combination of divalent metal ions and citrate," *Mol Pharm.*, 2012 9(3):554-62.

(Continued)

*Primary Examiner* — Kevin S Orwig
(74) *Attorney, Agent, or Firm* — Oblon, McClelland, Maier & Neustadt, L.L.P.

(57) ABSTRACT

The present disclosure includes a method of making an improved carbetocin drug product. The disclosed method for making an improved carbetocin drug product comprises agitating a carbetocin preparation containing an aqueous solution of carbetocin and one or more excipients for a period of time to initiate the formation of aggregate-forming solids and filtering off the aggregates that form before further processing the remaining carbetocin into a final drug product. The present disclosure also relates to an improved carbetocin drug product, wherein the drug product is substantially free of aggregate-forming solids. The disclosed carbetocin drug product can be used for the treatment of a neurodevelopmental disorder, such as Präder-Willi syndrome. Additionally, the disclosed carbetocin drug product shows content uniformity of carbetocin over long periods of time before and after one or more freeze/thaw cycles, provides enhanced convenience and patient compliance, and/or are highly concentrated.

9 Claims, 11 Drawing Sheets

(56) References Cited

U.S. PATENT DOCUMENTS

| | | |
|---|---|---|
| 2015/0216835 A1 | 8/2015 | Vath |
| 2015/0284434 A1 | 10/2015 | Bissantz et al. |
| 2016/0022726 A1 | 1/2016 | Feller et al. |
| 2017/0056364 A1 | 3/2017 | Vath |
| 2017/0081368 A1 | 3/2017 | Bissantz et al. |
| 2017/0081369 A1 | 3/2017 | Bissantz et al. |
| 2017/0106044 A1 | 4/2017 | Nilsson et al. |
| 2017/0174725 A1 | 6/2017 | Bleicher et al. |
| 2017/0232059 A1 | 8/2017 | Uvnäs-Moberg |
| 2017/0252546 A1 | 9/2017 | Park et al. |
| 2017/0304445 A1 | 10/2017 | Ogez et al. |
| 2017/0326200 A1 | 11/2017 | Danglas et al. |

FOREIGN PATENT DOCUMENTS

| | | |
|---|---|---|
| WO | WO 95/25534 | 9/1995 |
| WO | WO 2004/003145 | 1/2004 |
| WO | WO 2007/141541 | 12/2007 |
| WO | WO 2008/042452 | 4/2008 |
| WO | WO 2008/150305 | 12/2008 |
| WO | WO 2009/033782 | 3/2009 |
| WO | WO 2009/033783 | 3/2009 |
| WO | WO 2009/033820 | 3/2009 |
| WO | WO 2009/043457 | 4/2009 |
| WO | WO 2009/122285 | 10/2009 |
| WO | WO 2011/035330 | 3/2011 |
| WO | WO 2012/149472 | 3/2011 |
| WO | WO 2011/147889 | 12/2011 |
| WO | WO 2012/042371 | 4/2012 |
| WO | WO 2014/107231 | 4/2014 |
| WO | WO 2014/095773 | 6/2014 |
| WO | WO 2014/111356 | 7/2014 |
| WO | WO 2015/185467 | 12/2015 |
| WO | WO 2016/020349 | 2/2016 |
| WO | WO 2016/044131 | 3/2016 |
| WO | WO 2016/053091 | 4/2016 |
| WO | WO 2017/127287 | 7/2017 |
| WO | WO 2018/158234 | 7/2018 |

OTHER PUBLICATIONS

Avanti et al., "A new strategy to stabilize oxytocin in aqueous solutions: I. The effects of divalent metal ions and citrate buffer," *AAPSJ.* 2011, 13(2):284-290.

Avanti et al., "The Formation of Oxytocin Dimers is Suppressed by the Zinc-Aspartate-Oxytocin Complex," *Journal of Pharmaceutical Sciences*, (2013) vol. 102, 1734-1741.

Ayoub, Marwa, "Effect of some intranasal formulations used in the management of allergic rhinitis on mucociliary function," Thesis, University of Brighton, May 2015, 1-320.

Badiu and Marginean, "Current status and perspectives in the Treatment of Prader-Willi syndrome," *Expert Opinion on Orphan Drugs*, Apr. 2014, 2(4):337-347.

Baheti et al., "Excipients used in lyophilization of small molecules," *J. Excipients and Food Chem.* 1 (1) 2010, 42-54.

Bakermans-Kranenburg and Van Ijzendoorn, "Sniffing around oxytocin: review and meta-analyses of trials in healthy and clinical groups with implications for pharmacotherapy," *Translational Psychiatry*, 2013, 3:1-14.

Booth et al., "Hydrotrope accumulation around the drug: the driving force for solubilization and minimum hydrotrope concentration for nicotinamide and urea," *Phys. Chem. Chem. Phys.*, 2015, 17, 8028-8037.

Bueno Diez, "Prader-Willi syndrome and hyperphagia: A challenge to investigate," *Endocrinol. Nutr.*, 2014, 61:121-122.

Casettari, et al., "Chitosan in nasal delivery systems for therapeutic drugs," *Journal of Controlled Release* 190 (2014) 189-200.

Chapman et al., "Intranasal Treatment of Central Nervous System Dysfunction in Humans," *Pharmaceutical Research*, Oct. 2013, 30(10):2475-2484.

Cho et al., "Long-Term Use of Preservatives on Rat Nasal Respiratory Mucosa: Effects of Benzalkonium Chloride and Potassium Sorbate," *Laryngoscope* (2000) 110:312-317.

"Comparative Study Between Prader-Willi Patients Who Take Oxytocin Versus Placebo," NCT01038570 clinicaltrials.gov, University Hospital, Toulouse, Dec. 23, 2009.

Cromwell, M. E. M., et al. Protein aggregation and bioprocessing, AAPS J. (2006) 8(3); E572-E579.

"Current Solubilization Techniques: Insights from the BASF Solubilization Symposium," Feb. 2018.

DaSilva, et al., "Investigations on the mechanism of aqueous solubility increase caused by some hydrotropes," *Thermochimica Acta* 328 (1999) 161-167.

Damiati et al., "Application of machine learning in prediction of hydrotrope-enhanced solubilisation of indomethacin", *International Journal of Pharmaceutics* 530 (2017) 99-106.

De Berardis, G., "The Role of Intranasal Oxytocin in the Treatment of Patients with Schizophrenia: A Systematic Review," *CNS & Neurological Disorders—Drug Targets*, Mar. 2013, 12(2):252-264.

Deblon, "Mechanisms of the Anti-Obesity Effects of Oxytocin in Diet-Induced Obese Rats," PLoS ONE, Sep. 27, 2011, 6(9):e25565.

Declaration of Dr. Christopher Bryant under 37 C.F.R. § 1.132 submitted on Feb. 2, 2021, in U.S. Appl. No. 16/576,961.

Dhapte et al., "Advances in hydrotropic solutions: An updated review," St. Petersburg Polytechnical University Journal: Physics and Mathematics 1 (2015) 424-435.

Djupesland P.G., "Nasal drug delivery devices: characteristics and performance in a clinical perspective—a review," *Drug Deliv. and Transl. Res.* (2013) 3:42-62.

Drew et al., "Size estimation of chemical space: how big is it?" *J. Pharm. Pharmacol.*, 2012; 64(4):490-5.

Dua, R., "The Influence of Formulation and Device Variables on the Intranasal Absorption of Salmon Calcitonin," Open Access Dissertations, Paper 181, http://digitalcommonsuri.edu/oa_diss/181, (1995), 1-214.

Dutch Growth Research Foundation, "Intranasal administration of oxytocin in children and young adults with Prader-Willi Syndrome. A randomized, double-blind, placebo-controlled trial. Effects on satiety and food intake, and social behaviour," AdisInsight: Trials, Jul. 30, 2014.

Dykens EM et al., "Intranasal cabetocin reduces hyperphagia in induviduals with Prader-Willi syndrome," Published in vol. 3, Issue 12 on Jun. 21, 2018, *JCI Insight*. 2018;3(12):e98333, 1-11.

Eiholzer and Whitman, "A Comprehensive Team Approach to the Management of Patients with Prader-Willi Syndrome," Journal of Pediatric Endocrinology and Metabolism, Sep. 2004, 17(9):1153-1175.

Einfeld SL et al., "A Double-Blind Randomized Controlled Trial of Oxytocin Nasal Spray in Prader Willi Syndrome," *American Journal of Medical Genetics*, Part A, Sep. 2014, 164A(9):2232-9.

Elder, D.P., "Antimicrobial Preservatives Part Two: Choosing a Preservative," *American Pharmaceutical Review*, Jan. 1, 2012, 1-8.

"Evaluation of Tolerance, Suckling and Food Intake After Repeated Nasals Administrations of Oxytocin in PWS Infants," U.S. National Library of Medicine, ClinicalTrials.gov Identifier: NCT02205034, Last update May 12, 2017, https://clinicaltrials.gov/ct2/show/NCT02205034. Last accessed Jul. 11, 2020.

"Evaluation of Tolerance, Suckling and Food Intake After Repeated Nasals Administrations of Oxytocin in PWS Infants," NCT02205034 clinicaltrials.gov, University Hospital, Toulouse.

Fabio, et al., "Heat-Stable Dry Powder Oxytocin Formulations for Delivery by Oral Inhalation," *AAPS PharmSciTech*, vol. 16, No. 6, Dec. 2015, 1299-1306.

FDA, "Search orphan drug designations and approvals," https://www.accessdata.fda.gov/scripts/opdlisting/oopd/detailedIndex.cfm?cfgridkey=423014.

Frokjaer et al., "Protein drug stability: a formulation challenge," *Nat Rev Drug Discov.*, 2005; 4(4):298-306.

Gard et al., "Oxytocin preparation stability in several common obstetric intravenous solutions," *Am J Obstet Gynecol.*, 2002, 186(3):496-498.

(56) References Cited

OTHER PUBLICATIONS

Ghori et al., "Nasal Drug Delivery Systems: An Overview," *American Journal of Pharmacological Sciences*, 2015, vol. 3, No. 5, 110-119.
Goldstone, "Appetite hormones and the transition to hyperphagia in children with Prader-Willi syndrome," *International Journal of Obesity*, Dec. 2012, 36(12):1564-1570.
Goldstone, A.P. "Prader-Willi syndrome: advances in genetics, pathophysiology and treatment," *Trends in Endocrinology and Metabolism*, Jan. 2004-Feb. 2004, 15(1):12-20.
Härtl, Elisabeth Barbara, "Novel Approches for Stabilization and Characterization of Therapeutic Proteins in Liquid Formulations," Dissertation, Sep. 16, 2013, München, Germany.
Harris, "Therapeutic Interventions With Oxytocin: Current Stauts and Concerns," *Journal of the American Academy of Child & Adolescent Psychiatry*, Oct. 2013, 52(10):998-1000.
Hawe et al., "Towards heat-stable oxytocin formulations: analysis of degradation kinetics and identification of degradation products," *Pharm Res.*, 2009, 26(7):1679-88.
Heymsfield,"Hyperphagia: Current Concepts and Future Directions Proceedings of the 2nd International Conference on Hyperphagia," *Obesity*, 2014, 22:S1-S17.
Ho, "Coming Full Circle: Contributions of Central and Peripheral Oxytocin Actions to Energy Balance," *Endocrinology*, Feb. 2013, 154(2):589-596.
Hofmann et al., "Influence of Preservatives and Topical Steroids on Ciliary Beat Frequency In Vitro," *Arch Otolaryngol Head Neck Surg*, vol. 130, Apr. 2004, 130:440-445.
Hofmann et al., "Predictive Screening Tools Used in High-Concentration Protein Formulation Development," *J. Pharm. Sci.*, 107 (2018) 772-777.
Hodgdon, T.K. and Kaler, EW., "Hydrotropic solutions," *Curr. Opin. in Colloid & Interface Sci.* 2007;12(3):121-128.
Høgstedt, U.B., "Formulation of concentrated peptide solutions—physical stability challenges and the impact on peptide-peptide interactions," *Industrial PhD Thesis*, submitted to the Graduate School of the Faculty of Health and Medicinal Sciences, University of Copenhagen. Copenhagen, Nov. 2017.
Høgstedt et al., "Manipulating Aggregation Behavior of the Uncharged Peptide Carbetocin," *J. Pharm. Sci.*, 2018, 107(3):838-847.
Hollan, A., "Understanding the eating disorder affecting people with Prader-Willi syndrome," *Journal of Applied Research in Intellectual Disabilities*, 1998, 11(3):192-206.
Hung, Nguyen Ba, "Sequence dependent aggregation of peptides and fibril formation," *J. Chem. Phys.* 147, 2017, 105102-1 to 105102-10.
International Search Report for International Application No. PCT/US19/52090, dated Nov. 21, 2019.
International Search Report for International Application No. PCT/US19/52092, dated Nov. 20, 2019.
Kaal, Andreas et al., "Occurence and effects of octreotide antibodies during nasal, subcutaneous and slow release intramuscular treatment," *European Journal of Endocrinology* (2000) 143 353-361.
Kelly and Feifel, "Emerging Clinical Evidence on Oxytocin in Schizophrenia," (abstract), *Schizophrenia Research*, Apr. 2012, 136(Supp. 1):S69.
Kheddo et al., "The Effect of arginine glutamate on the stability of monoclonal antibodies in solution," *International Journal of Pharmaceutics*, 473 (2014) 126-133.
Kiese et al., "Shaken, Not Stirred: Mechanical Stress Testing of An IgG1 Antibody," *J. Pharm. Sci.*, 2008, 97(10):4347-66.
Kin et al., "Hydrotropic Solubilization of Poorly Water-Soluble Drugs," *Journal of Pharmaceutical Sciences*, vol. 99, No. 9, Sep. 2010, 3953-3965.
Koepf et al., "Notorious but not understood: How liquid-air interfacial stress triggers protein aggregation," *International Journal of Pharmaceutics*, 537 (2018) 202-212.
Ku, Sherry, "Solutol Hs15 as a Novel Excipient," *Pharmaceutical Technology*, vol. 34, Issue 11, 108-110.
Kumar et al., "Nasal-nanotechnology: revolution for efficient therapeutics delivery," (2016), *Drug Delivery*, 23:3, 671-683.
Li et al., Non-ionic surfactants as novel intranasal absorption enhancers: in vitro and in vivo characterization, *Drug Delivery*, (2016), 23:7, 2272-2279.
Madan et al., "Solubility enhancement studies on lurasidone hydrochloride using mixed hydrotropy," *International Journal of Pharmaceutical Investigation*, Apr. 2015, vol. 5, Issue 2, 114-120.
Maddux et al., "Microflow Imaging Analyses Reflect Mechanisms of Aggregate Formation: Comparing Protein Particle Data Sets Using the Kullback-Leibler Divergence," *J. Pharm. Sci.*, 106 (2017) 1239-1248.
Manning et al., "Peptide and non-peptide agonists and antagonists for the vasopressin and oxytocin V1a, V1b, V2 and OT receptors: research tools and potential therapeutic agents," *Prog Brain Res*, 2008, 170:473-512.
Marazziti et al., "The Role of Oxytocin in Neuropsychiatric Disorders," *Current Medicinal Chemistry*, 2008, 15(7):698-704.
Martin et al., "Efficacy, Safety and Mechanism of Cyclodextrins as Absorption Enhancers in Nasal Delivery of Peptide and Protein Drugs," *Journal of Drug Targeting*, 6:1, 17-36 (1998).
Mathaes et al., "Application of different analytical methods for the characterization of non-spherical micro- and nanoparticles," *International Journal of Pharmaceutics*, 453 (2013) 620-629.
Mcallister, "Development of the eating behaviour in Prader-Willi Syndrome: advances in our understanding," *International Journal of Obesity*, Feb. 2011, 35(2):188-97.
Meredith et al., "Intranasal Delivery of Proteins and Peptides in the Treatment of Neurodegenerative Diseases," *The AAPS Journal*, vol. 17, No. 4, Jul. 2015, 780-787.
Merkus, P., "Current aspects of nasal drug delivery," Dissertation, (2006), 1-181.
Mitesh et al., "Formulation of carbetocin injection by lyophilization technique," Der Pharmacia Lettre, 2013 5 (5): 200-205.
Moharil et al., "Nasal Dosage Forms and Devices for Intranasal Drug Delivery," *World Journal of Pharmacy and Pharmaceutical Sciences*, vol. 3, Issue 4, 554-571.
Murtaza et al., "Comparative evaluation of various solubility enhancement strategies for furosemide," *Pak. J. Pharm. Sci.*, vol. 27, No. 4, Jul. 2014, pp. 963-973.
NewsRx, "Chu De Toulouse; Agency Reviews Patent Application Approval Request for Methods and Pharmaceutical Composition for the Treatment of a Feeding Disorder with Early-Onset in a Patient," *Genetics & Environmentla Law Weekly* [Atlanta], May 18, 2013):225.
NewsRx, "Clinical Research; Findings in the Area of Clinical Trials and Studies Reported from University of Sydney (A Double-Blind Randomized Controlled Trial of Oxytocin Nasal Spray in Prader Willi Syndrome) (A Double-Blind Randomized Controlled Trial of Oxytocin Nasal), " *Biotech Week* [Atlanta] (Sep. 24, 2014): 481.
Nucci et al., "Carbetocin for prevention of postcesarean hemorrhage in women with severe preeclampsia; a before-after cohort comparison with oxytocin," *J. Clin. Anesth.*, 2016, 35:321-325.
Olszewski et al., "Oxytocin as Feeding Inhibitor: Maintaining Homeostasis in Consummatroy Behavior," *Pharmacology Biochemistry and Behavior*, Nov. 2010, 97(1):47-54.
Onaka, Jichi, "Roles of Oxytocin Neurones in the Control of Stress, Energy Metabolism, and Social Behaviour," *Journal of Endocrinology*, Apr. 2012, 24:587-598.
Ott, "Oxytocin Reduces Reward-Driven Food Intake in Humans," *Diabetes*, Oct. 2013, 62(10):3418-3425.
"Oxytocin Trial in Prader-Willi Syndrome," NCT02013258 clinicaltrials. gov, University of Florida.
Panganiban et al., "Random heteropolymers preserve protein function in foreign environments," *Science* 359, 1239-1243 (2018).
Pathak K., "Muciadhesion; A prerequisite or a constraint in nasal drug delivery?" *Int J Pharm Investig.*, 2011, 1(2):62-3.
Payne R. W. et al., "Second virial coefficitent determination of a therapeutic peptide by self-interaction chromatography," *Biopolymers*, 2006, 84:527-533.
Pollack, "Seeking Clues ti Obesity in Rare Hunger Disorder: [Business/Financial Desk]," *New York Times*, Late Edition (East Coast) [New York, N.Y] (Jan. 15, 2014): B.1.

(56) References Cited

OTHER PUBLICATIONS

Poole et al., "Formation of Amide- and Imide-Linked Degradationg Products Between the Peptide Drug Oxytocin and Citrate in Citrate-Buffered Formultions," *Journal of Pharmaceutical Sciences*, vol. 100, No. 7, Jul. 2011.
Pu et al., "A Comparison of the Deposition Patterns of different Nasal Spray Formulations Using a Nasal Cast," *Aerosol Science and Technology*, 48:930-938, 2014.
"Public summary of opinion on orphan designation. Carbetocin for the treatment of Prader-Willi syndrome," Public summary of opinion on orphan designation EMA/COMP/69949/2012.
Quintana et al., "Evidence for intranasal oxytocin delivery to the brain: recent advances and future perspectives," *Ther. Deliv.* (2018) 9(7), 515-525.
Roberts, Christopher J., "Therapeutic Protein Aggregation: Mechanisms, Design, and Control," *Trends Biotechnol.* Jul. 2014; 32(7): 372-380.
Schaller, "A single postnatal injection of oxytocin rescues the lethal feeding behaviour in mouse newborns deficient for the imprinted Magel2 gene," *Human Molecular Genetics*, Dec. 15, 2010, 19(24):4895-905.
Schreier et al., "Surface active drugs: self-association and interaction with membranes and surfactants. Physicochemical and biological aspects," *Biochimica et Biophysica Acta* 1508 (2000) 210-234.
Shah et al., "Nasal Delivery of Proteins and Peptides," *Glob J Pharmaceu Sci*, vol. 1, Issue 4, Apr. 2017, 1-3.
Shimizu et al., "Hydrotropy: Monomer—Micelle Equilibrium and Minimum Hydrotrope Concentration," *J. Phys. Chem.* B 2014, 118, 10515-10524.
Shire et al., "Challenges in teh development of high protein concentration formulations," *J Pharm Sci.*, 2004, 93:1390-1402.
Smith et al., "Prader-Willis Syndrome [PWS]—Is Behavioral Modification Possible?", (abstract), *Twin Research and Human Genetics*, Aug. 2011, 14(4):350-351.
Striepens et al., "Prococial effects of oxytocin and clinical evidence for its therapeutic potential," *Fronteirs in Neuroendocrinology*, Oct. 2011, 32(4):426-450.
Swaab, "Neuropeptides in Hypothalamic Neuronal Disorders," Jeon, KW [Editor]. *Int. Rev. Cytol.*, 2004, pp. 305-375.
Tauber, et al., "Oxytocin may be useful to increase trust in others and decrease disruptive behaviours in patients with Prader-Willi syndrome: a randomised placebo-controlled trial in 24 patients," *Orphanet Journal of Rare Diseases*, Jun. 24, 2011, 6:47.
Terne, F., NMR Study on the Aggregation Behavior of the Therapeutic Peptide Carbetocin, *Master Thesis in Pharmaceutical Technology*, Lund University, 2018.
Teng et al., "Comparison of effectiveness and safety of carbetocin and oxytocin for prevention of postpartum hemorrhage after cesarean section," *Shengzhi Yixue Zazhi*, 2007, 16(2), 73-76.
Teng et al., "Study of drug control over postoperative hemorrhage after selective caesaraen section," *J. Reprod. Med.*, 2006, vol. 15, 48-52.
"Tolerance of Intranasal Administration of OT in Prader-Willi Newborn Babies," NCT01548521 clinicaltrials.gov, Universoty Hospital, Toulouse.
Trows, et al., "Analytical Challenges and Regulatory Requirements for Nasal Drug Products in Europe and the U.S.," *Pharmaceutics* 2014, 6, 195-219.
Unterrrainer et al., "Caesarean section and brain tumour resection," *Br J. Anaesth.*, Jul. 2011;107(1):111-2.

VerticalNews.com, "Prader-Willi Syndrome; Oxytocin promises hope in Prader-Willi syndrome," *NewsRx Health & Science* [Atlanta], Jul. 17, 2011, 194.
Warnken et al., "Formulation and device design to increae nose to brain drug delivery," *Journal of Drug Delivery Science and Technology* 35 (2016) 213-222.
Whitaker et al., "A Formulation Development Approach to Identify and Select Stable Ultra-High-Concentration Monoclonal Antibody Formulations With Reduced Viscosities," *J. Pharm. Sci.*, 106 (2017) 3230-3241.
Widmer et al., "Room temperature stable carbetocin for the prevention of postpartum haemorrhage during the third stage of labour in women delivering vaginally: study protocol for a randomized controlled trial." *Trials*, 2016 17:143.
Williams et al., "In vitro and preclinical assessment of an intranasal spray formulation of parathyroid hormone PTH 1-34 for the treatment of osteoporosis," *International Journal of Pharmaceutics* 535 (2018) 113-119.
Written Opinion of the International Search Authority for International Application No. PCT/US19/52090, dated Nov. 21, 2019.
Written Opinion of the International Search Authority for International Application No. PCT/US19/52092, dated Nov. 20, 2019.
Yarragudi, S.B., "Formulation Strategies to Enhance Nose-to-Brain Delivery of Drugs," Thesis, Univeristy of Otago Duedin, New Zealand, Jun. 2018, 1-256.
Yang, M., Jun. 1, 2015; BioPharm International. Accessed Oct. 2, 2020 at https://www.biopharminternational.com/view/stress-and-protein-instability-during-formulaiton-andfillfinish-processes.
Zapadka K.L. et al. Factors affecting the physical stability (aggregation) of peptide therapeutics. *Interface Focus*, pp. 1-18, 2017;7(6).
Benelli, et al., "Polymodal Dose-responsive Curve for Oxytocin in the Social Recognition Test" Neuropeptides (1995) 28, pp. 251-255.
Cardoso, et al., "Intranasal oxytocin attenuates the cortisol response to physical stress: A dose-response study" (Psychoneuroendocrinology (2013) 38, pp. 399-407.
Chen, et al., "Oxytocin modulates human chemosensory decoding of sex in a dose-dependent manner" eLife (2021) 10:e59376. DOI: https://doi.org/10.7554/eLife.59376.
Hall, et al., "Effects of intranasal oxytocin on social anxiety in males with fragile X syndrome" Psychoneuroendocrinology (2012) 37, pp. 508-518.
Martins, et al., "Effects of route of administration on oxytocin-induced changes in regional cerebral blood flow in humans" Nature Communications (2020) https://doi.org/10.1038/s41467-020-14845-5.
Popik, et. al., "Low doses of oxytocin facilitate social recognition in rats" Psychopharmacology (1992) 106, pp. 71-74.
Quintana, et al., "Low-dose oxytocin delivered intranasally with Breath Powered device affects social-cognitive behavior: a randomized four-way crossover trial with nasal cavity dimension assessment" Transl. Psychiatry (2015) 5, pp. 1-9, e602; doi:10.1038/tp.2015.93.
Quintana, et al., Low dose intranasal oxytocin delivered with Breath Powered device dampens amygdala response to emotioinal stimuli: A peripheral effect-controlled within-subjects randomized dose-response fMRI trial, Psychoneuroendocrinology (2016) 69 pp. 180-188.
Quintana, et al., "Dose-dependent social-cognitive effects of intranasal oxytocin delivered with novel Breath Powered device in adults with autism spectrum disorder: a randomized placebo-controlled double-blind crossover trial" Transl. Psychiatry (2017) 7, pp. 1-9, e1136; doi:10.1038/tp.2017.103.
Spengler, et al., "Kinetics and Dose Dependency of Intranasal Oxytocin Effects on Amygdala Reactivity" Biological Psychiatry (Dec. 15, 2017) 82, pp. 885-894.

AGITATION PROCESS FOR PREPARING A CARBETOCIN DRUG PRODUCT

DESCRIPTION OF THE DISCLOSURE

This application is a divisional of U.S. patent application Ser. No. 17/529,861, filed Nov. 18, 2021, which is a divisional of U.S. patent application Ser. No. 16/576,961, filed Sep. 20, 2019, and issued Dec. 28, 2021, as U.S. patent Ser. No. 11,207,373, which claims the benefit of priority to U.S. Provisional Patent Application No. 62/876,870, filed Jul. 22, 2019, and U.S. Provisional Patent Application No. 62/734,134, filed Sep. 20, 2018, all of which are incorporated herein by reference.

FIELD OF THE DISCLOSURE

This disclosure relates to a method of making an improved carbetocin drug product and an improved carbetocin drug product itself, including those that are free of visible particles and/or resistant to aggregation. This disclosure further relates to the use of such preparations in methods of treating diseases and conditions that are beneficially treated by administering carbetocin to a subject in need thereof.

BACKGROUND OF THE DISCLOSURE

Although both peptides and proteins are composed of amino acids, peptides are typically distinguished from proteins as having a shorter amino acid sequence, such as, for example, less than 50 amino acids. Because of this difference in size, peptides and proteins often possess different three-dimensional structures, properties, and functions. Peptides are used to treat various diseases and conditions.

Depending on potency, it may be necessary to formulate a peptide at a high concentration, but doing so may increase the likelihood of peptide aggregation. (Shire S. J. et al. (2004) J Pharm Sci. 93:1390-1402; Payne R. W. et al. (2006) Biopolymers 84:527-533.) One way to mitigate peptide aggregation is to formulate the peptide at a pH far from its isoelectric point to generate a high net charge. But for peptides without ionizable groups, pH optimization may not be possible. Consequently, maintaining a sufficient stability at high peptide concentrations may be challenging, especially since peptides generally do not possess higher-order structure, and their physical stability thus primarily depends on the nature of their peptide-peptide interactions. Peptides in solution may also degrade via, e.g., deamidation, oligomerization, and oxidation, making refrigeration in some cases necessary.

Carbetocin [(1-desamino-1-monocarba-2(O-methyl)-tyrosine) oxytocin] is an example of an uncharged peptide. Carbetocin is a long-acting synthetic oxytocin analog. The structure of carbetocin is shown below.

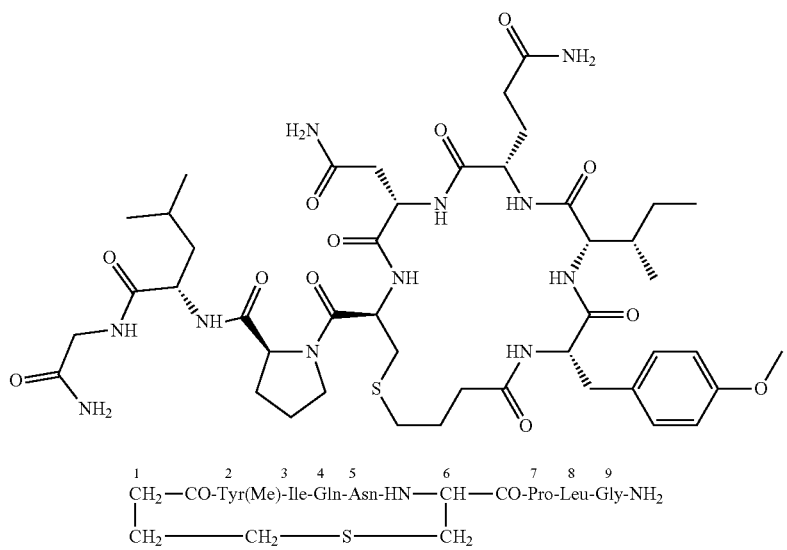

Carbetocin is an unusual peptide: it is small (8 amino acids); possesses no charge, is cyclic, and is highly lipophilic. It is also known that carbetocin lacks a stable and well-defined tertiary structure. Carbetocin is currently used outside the U.S. to treat or prevent postpartum hemorrhage during caesarean section. As such, carbetocin is administered by slow intravenous (IV) single injection at a dose of 100 μg. This formulation (Duratocin®, Ferring) requires refrigeration and contains 0.1 mg/mL of carbetocin, 9 mg sodium chloride, acetic acid—glacial to pH 3.8 and water for injection to 1 mL. (Widmer M. et al. (2016) Trials. 17:143.) Carbetocin (IV form) is currently registered in more than 70 countries under the trade names PABAL/DURATOCIN/LONACTENE/DURATOBAL.

Another injectable carbetocin drug product currently in clinical trials, CARBETOCIN RTS, can be stored at 30° C. for at least 3 years. (Widmer M. et al. (2016) Trials. 17:143.) Other prior attempts to develop a heat-stable oxytocin formulation for injection have been unsuccessful. (Hawe A. et al. (2009) Pharm Res. 26(7):1679-1688; Avanti C. et al. (2012) Mol Pharm. 9(3):554-562; Avanti C. et al. (2011) AAPSJ. 13(2):284-290; Gard J. W. et al. (2002) Am J Obstet Gynecol. 186(3):496-498.) This room temperature stable (RTS) variant of carbetocin has recently been developed and is now approved in the European Union; this variant differs from the current carbetocin formulation in its excipients. CARBETOCIN RTS contains 0.1 mg/mL of carbetocin, 1.19 succinic acid, 47.0 mg/mL mannitol, 1 mg/mL L-methionine, sodium hydroxide 2N to pH 5.45, and water for injection to 1 mL. (Widmer M. et al. (2016) Trials. 17:143.)

Attempts have been made to make stable high carbetocin formulations using typical peptide excipients (e.g., surfactants); however, none of the studied excipients prevented carbetocin aggregation. (Høgstedt U. B. et al. (2018). J Pharm Sci. 107(3):838-847.) Only in the absence of headspace was 15 mM sodium dodecyl sulfate (SDS) capable of preventing shaking induced carbetocin aggregation.

In addition, when aqueous carbetocin solutions are manufactured, packaged, transported, stored, and handled prior to administration to a patient, they are subject to mechanical and chemical stresses. These types of stresses can be detrimental to various formulations of carbetocin in solution.

Given the propensity of carbetocin to aggregate in solution, a stable drug product formulation that optimizes and extends carbetocin's in-use period, as well as delivers relatively high content uniformity is desirable. For example, an intranasal formulation that can be thawed by a patient and used for several days without aggregation or a change in the carbetocin content from one dose to another would enhance patient compliance and safety.

There is thus a need for a stable and uniform formulation of carbetocin that can be stored for long periods of time, including at a temperature below freezing, and then thawed and used for several days, if not a week, of patient in-use time.

In addition, a stable high concentration pharmaceutical preparation of carbetocin is advantageous because a higher concentration of carbetocin could be formulated in, for example, a restricted injection volume of, for example, <1.5 mL. This is important, for example, when the potency of the active at lower concentrations does not provide the desired pharmacological effect, and it may be necessary to formulate carbetocin at a higher concentration. Thus, a higher concentration of carbetocin in solution could have a higher therapeutic relevance as it would further increase, for example, the biological effect of carbetocin on a subject, and would further provide enhanced convenience and patient compliance.

Given carbetocin's strong propensity to aggregate in solution, there remains a need for improved processes to make stable carbetocin pharmaceutical preparations, including those that are stable to stress, suitable for various routes of administration (e.g., intravenous, subcutaneous (s.c.), intramuscular, and intranasal routes of administration), show content uniformity of carbetocin over long periods of time before and after one or more freeze/thaw cycles, provide enhanced convenience and patient compliance, and/or are highly concentrated.

SUMMARY OF THE DISCLOSURE

It has been surprisingly found that an improved carbetocin pharmaceutical preparation (i.e., carbetocin drug product) can be prepared by a process comprising agitating a carbetocin preparation containing an aqueous solution of carbetocin and one or more excipients for a period of time to initiate formation of aggregates and filtering off the aggregates that form ("aggregate-forming solids") before further processing the remaining carbetocin preparation into a final drug product. In one embodiment, the method uses certain solubilizers and/or surface active agents, such as a viscoelastic polymer, for example, hydroxypropyl methylcellulose (HPMC), including those that contain high concentrations of carbetocin and that are stable under conditions of stress. This disclosure provides a method of obtaining a preparation comprising a clear solution of carbetocin, which is stable after conditions of stress, including after thawing of a final drug product for patient use. In some embodiments, the improved carbetocin preparation made by the disclosed process is resistant to aggregation for long periods of time when subjected to, for example, continuous agitation or one or more freeze/thaw cycles.

For example, the disclosure provides a method for making and a carbetocin drug product that remains unexpectedly stable even at relatively high concentrations of carbetocin (e.g., greater than about 10 mg/mL to about 70 mg/mL) and under accelerated stress conditions. In some embodiments of the present disclosure, the method uses an active pharmaceutical ingredient, i.e., carbetocin, to make a pharmaceutical preparation in a high concentration of at least 10 mg/mL, which is 100 times greater than that of the DURATOCIN® and CARBETOCIN RTS products referenced above. In other embodiments of the present disclosure, carbetocin is present in a pharmaceutical preparation in a concentration of at least 34.3 mg/mL, which is 343 times greater than that of the DURATOCIN® and CARBETOCIN RTS products.

In at least one embodiment, the present disclosure provides a method for making a carbetocin drug product comprising an aqueous solution of carbetocin and a solubilizer and/or surface active agent, wherein the resulting carbetocin drug product exhibits a high content uniformity of carbetocin for long periods of time not only at room temperature, but also after freezing and thawing. In at least one embodiment, the carbetocin drug product of the present disclosure is substantially free of aggregate-forming solids.

For example, the disclosed carbetocin drug product shows content uniformity of carbetocin after thawing for 3-7 days (longer shelf life and/or in-use period). In at least some embodiments, the method for making a carbetocin drug product provides an improved carbetocin drug product that is stable and does not aggregate for a period of time after one or more freeze/thaw cycles. In some embodiments, the carbetocin drug product of the disclosure has little to no aggregate-forming solids by visual assessment, which may include photographs. In some embodiments, the carbetocin in the disclosed preparation is evenly distributed throughout the preparation to ensure that if the preparation is, for example, split in one or more preparations, each resulting preparation has an equal dose of carbetocin. In one embodiment, the disclosed carbetocin drug product has a consistent (i.e., uniform) dose of carbetocin, which is maintained between various batches so that the patient receives the correct dose consistently over various administrations. In at least one embodiment, the disclosed carbetocin drug product provides enhanced convenience and patient compliance.

In certain embodiments, the disclosure provides a method for making a carbetocin drug product (and a carbetocin drug product itself) comprising an aqueous solution of carbetocin and at least one solubilizer and/or surface active agent chosen from cyclodextrins, hydrotropes, amino acids, and/or cellulose derivatives. In at least one embodiment, the carbetocin drug product does not include a surfactant (e.g., n-dodecyl-13-D-maltoside (DDM), poloxamer 188, polysorbate 20 or polysorbate 80, sodium dodecyl sulfate). In at least one embodiment, the carbetocin drug product does not have reduced headspace, i.e., the container is not completely full.

In at least one embodiment, the disclosure provides a method for making a carbetocin drug product (and a carbetocin drug product itself) comprising an aqueous solution of carbetocin and a hydrotrope and/or HPMC, wherein the solution has no visible solids (i.e., aggregate-forming solids) after being subjected to agitation stress conditions. Such a preparation may be sufficiently stable even under conditions of stress (e.g., shaking and stirring, pumping, freeze-thaw processes) for extended periods of time with little to no visible solids. In at least some embodiments, the carbetocin drug product has little to no aggregate-forming solids by visual assessment, including via photograph. In some embodiments, the carbetocin drug product exhibits no visible solids when inspected visually after a period of 24 hours after continuous shaking.

Without wishing to be bound by any particular theory, it is believed that the aggregate-forming solids generated by the agitation of carbetocin in an aqueous solution are initially comprised of a minuscule amount of aggregated carbetocin type molecules (e.g., an increased amount of R-sheet structure which is typically associated with peptide aggregation; fibril formation), which initiate the original precipitation event, and ultimately these aggregates may precipitate all the carbetocin in the preparation if not removed within a period of time. It is also believed that removal of these aggregate-forming solids eliminates carbetocin molecules with a propensity to aggregate and lowers the likelihood that the remaining carbetocin in the drug product will aggregate.

In at least one embodiment, the concentration of carbetocin ranges from about 1 mg/mL to about 70 mg/mL. In at least one embodiment, the concentration of carbetocin ranges from about 1 mg/mL to about 70 mg/mL. In at least one embodiment, the concentration of carbetocin ranges from about 5 mg/mL to about 36 mg/mL. In at least one embodiment, the concentration of carbetocin is about 34.3 mg/mL. In at least one embodiment, the concentration of carbetocin is about 11.4 mg/mL. In some embodiments, the high concentration carbetocin drug product has no visible solids when stored at room temperature (e.g., 25° C.) for a sustained period of time. For example, the carbetocin drug product has no visible solids for up to 3 years. In some embodiments, the carbetocin drug product has no visible solids for 2 years. In some embodiments, the carbetocin drug product has no visible solids for 1 year. In some embodiments, the carbetocin drug product has no visible solids for up to 3 years when the headspace is near zero. In one embodiment, carbetocin drug product has no visible solids for up to 3 years when the headspace is substantially zero. In some embodiments, the carbetocin drug product exhibits no visible solids when inspected visually after a period of 24 hours after continuous shaking.

In at least one embodiment, carbetocin is not subject to chemical degradation as measured by HPLC. For example, the chromatographic purity of carbetocin is greater than 97%. In at least one embodiment, the chromatographic purity of carbetocin is greater than 98%. In at least one embodiment, the chromatographic purity of carbetocin is greater than 99%. In at least one embodiment, the chromatographic purity of carbetocin is greater than 99.5%.

In at least one embodiment, the disclosure provides a method for making a pharmaceutical preparation, for example, a carbetocin drug product, that is stable to shaking stress. In some embodiments, the preparation is subjected to shaking stress for at least 24 hours, and the aqueous carbetocin solution remains clear with little to no visible particles. In at least one embodiment, carbetocin does not chemically degrade before or after shaking stress. For example, the chromatographic purity of carbetocin is greater than 98%. In at least one embodiment, the chromatographic purity of carbetocin is greater than 99%. In at least one embodiment, the chromatographic purity of carbetocin is ≥99.5. Such chromatographic purity occurs with and without exposure to shaking stress.

The carbetocin drug product comprises at least one surface active agent and/or solubilizer chosen from a hydrotrope, a cyclodextrin, amino acid, and/or a cellulose derivative.

If present in the carbetocin drug product, the hydrotrope may be chosen from an aromatic anionic compound, aromatic cationic compound, or an aliphatic, linear compound. In some embodiments, the aromatic anionic compound is chosen from sodium benzoate, salicylate salts, sodium benzene sulfonate, sodium benzene disulfonate, sodium cinnamate, sodium 3-hydroxy-2-naphthoate, sodium para-toluene sulfonate, sodium cumene sulfonate, nicotinamide, N,N-diethylnicotinamide, or N,N-dimethyl benzamide. In one embodiment, the hydrotrope is nicotinamide. In some embodiments, the aromatic cationic compound is chosen from para-aminobenzoic acid hydrochloride, procaine hydrochloride, or caffeine. In other embodiments, the aliphatic, linear compound is chosen from sodium alkanoate, urea, or N,N-dimethyl urea. In at least one embodiment, the hydrotrope is selected from the group consisting of nicotinamide, sodium benzoate, and salicylate salts (e.g., sodium salicylate, potassium salicylate, lithium salicylate, ammonium salicylate, calcium salicylate, and magnesium salicylate).

If present in the carbetocin drug product, the amino acid may be chosen from a natural or unnatural amino acid. In one embodiment, the natural amino acid is arginine.

If present in the carbetocin drug product, nicotinamide is present in a concentration ranging from 50 mM to 500 mM. In at least one embodiment, the concentration of nicotinamide is about 400 mM. In at least one embodiment, the concentration of nicotinamide is about 300 mM. In another embodiment, the concentration of nicotinamide is about 200 mM.

If present in the carbetocin drug product, the solubilizer may be chosen from a cyclodextrin derivative. In at least some embodiments, the cyclodextrin derivative is chosen from methyl-β-cyclodextrin, randomly methylated-β-cyclodextrin (RM-β-CD), sulfobutylether-β-cyclodextrin (SBE-β-CD), epichlorohydrin-A-cyclodextrin, and carboxy methyl epichlorohydrin beta cyclodextrin. In some embodiments, the cyclodextrin derivative is methyl-β-cyclodextrin.

If present in the carbetocin drug product, the surface active agent may be chosen from a viscoelastic polymer, such as HPMC. In at least some embodiments, the surface active agent is a cellulose derivative. In at least one embodiment, the cellulose derivative may be chosen from hydroxypropyl cellulose (HPC), hydroxypropyl methylcellulose (HPMC), and carboxy methyl ethyl cellulose (CMEC). In some embodiments, the cellulose derivative is HPMC.

If present in the carbetocin drug product, HPMC is present in an amount ranging from 0.005% to 0.05% w/v. In at least one embodiment, HPMC is present in an amount ranging from 0.0075% to 0.0125% w/v. And, in some embodiments, HPMC is present in an amount ranging from 0.0075% to 0.01% w/v. In at least one embodiment, HPMC is high viscosity grade. In at least one embodiment, the high viscosity HPMC is 4000 cP.

In at least some embodiments, there is provided a method for making a carbetocin drug product comprising HPMC and/or nicotinimide.

In some embodiments, the carbetocin drug product further comprises a tonicity enhancer (excipient) to adjust the osmolality from about 220 mOsm/Kg to about 370 mOsm/Kg. In at least one embodiment, the osmolality is about 225 mOsm/Kg. In at least one embodiment, the osmolality is about 290 mOsm/Kg. In at least one embodiment, the osmolality is about 352 mOsm/Kg. In at least one embodiment, the osmolality is about 370 mOsm/Kg. In at least one embodiment, the tonicity enhancer is sorbitol. In some embodiments, sorbitol is present in a concentration ranging from 100 mM to 287 mM. In at least one embodiment, the concentration of sorbitol is about 110 mM. In at least one embodiment, the concentration of sorbitol is about 130 mM.

In at least one embodiment, the pH of the carbetocin pharmaceutical preparation ranges from 3.0 to 6.3, for example, from 3.35 to 6.07, from 5.4 to 5.8, or 5.4 to 5.45. In at least one embodiment, the pH is 5.4±0.5. In another embodiment, the pH is 5.4±0.3. In one embodiment, the pH is about 5.4±0.1.

The carbetocin drug product disclosed herein may be formulated in a container. The container may be chosen from a glass beaker, volumetric flask, an ampoule, vial, or pre-filled intranasal delivery device. In at least one embodiment, the vial is a scintillation vial.

In some embodiments, the method of making a carbetocin drug product comprises a polar protic solvent. In one embodiment the solvent is water. Water can be, but is not limited to, water for injection ("WFI"), highly purified water ("HPW"), and purified water ("PW").

In at least one embodiment, the method for preparing a carbetocin drug product comprises:
(a) agitating an aqueous solution comprising carbetocin and one or more excipients;
(b) allowing aggregate-forming solids to form; and
(c) removing the formed aggregate-forming solids.

In at least one embodiment, the resulting carbetocin drug product is substantially free of the aggregate-forming solids. In some embodiments, the concentration of carbetocin in the carbetocin drug product ranges from about 1 mg/mL to about 70 mg/mL.

In at least one embodiment, the method for preparing a carbetocin drug product comprises:
(a) adding water to a container and stirring the water preparation;
(b) adding at least one solubilizer and/or surface active agent to the preparation of step (a) and optionally adding one or more excipients to the preparation to adjust osmolality;
(c) adding carbetocin to the preparation of step (b) until carbetocin is completely dissolved in solution and optionally adjusting the solution to a target volume with water, and further filtering the solution to obtain a pre-agitation preparation, wherein the solution has a pH ranging from about 3.00 to about 6.26.
(d) agitating the preparation from step (c) for a period of time to induce aggregate-forming solids to formand filtering off the aggregate-forming solids from the carbetocin preparation; and
(e) saving the filtrate that is free of the aggregate-forming solids in a container to obtain a post-agitation carbetocin drug product, wherein the carbetocin drug product is substantially free of the aggregate-forming solids.

In at least one embodiment, the water used in step (a) is water for injection ("WFI") or purified water. In one embodiment, the water is WFI.

In at least one embodiment, the disclosed process provides for improved carbetocin drug products that may be administered intravenously, subcutaneously (s.c.), intramuscularly, and intranasally, such as for example, daily, for a period of time. In one embodiment, the carbetocin drug product is administered intranasally.

In at least one embodiment, a carbetocin drug product is an aqueous drug product comprising carbetocin and a pharmaceutically acceptable excipient, wherein the carbetocin drug product is substantially free of aggregate-forming solids.

In at least one embodiment, a carbetocin drug product comprises:
(a) carbetocin, wherein the carbetocin is present in a concentration of bout 34.3 mg/mL;
(b) nicotinamide, wherein the nicotinamide is present in a concentration of about 200 mM;
(c) HPMC, wherein the HPMC is present in an amount of about 0.01% w/v; and
(d) sorbitol, wherein the sorbitol is present in a concentration ranging from about 100 mM to about 200 mM.

In at least one embodiment, a carbetocin drug product comprises:
(a) carbetocin, wherein the carbetocin is present in a concentration of about 34.3 mg/mL;
(b) nicotinamide, wherein the nicotinamide is present in a concentration of about 200 mM;
(c) HPMC, wherein the HPMC is present in an amount of about 0.0075%; and
(d) sorbitol, wherein the sorbitol is present in a concentration of about 110 mM.

In at least one embodiment, a carbetocin drug product comprises:
(a) carbetocin, wherein the carbetocin is present in a concentration of about 34.3 mg/mL;
(b) nicotinamide, wherein the nicotinamide is present in a concentration of about 200 mM;
(c) HPMC, wherein the HPMC is present in an amount of about 0.01%; and
(d) sorbitol, wherein the sorbitol is present in a concentration of about 110 mM.

In at least one embodiment, a carbetocin drug product comprises:
(a) carbetocin, wherein the carbetocin is present in a concentration of about 11.4 mg/mL;
(b) nicotinamide, wherein the nicotinamide is present in a concentration of about 200 mM;
(c) HPMC, wherein the HPMC is present in an amount of about 0.01%; and
(d) sorbitol, wherein the sorbitol is present in a concentration of about 110 mM.

In at least some embodiments, the disclosed improved carbetocin drug products may be for use in (or in the manufacture of medicaments for) the treatment or prevention of a neurodevelopmental disorder or related symptoms in a subject in need thereof. In at least one embodiment, a therapeutically-effective amount of a carbetocin drug product of the present disclosure is administered to a subject diagnosed with Präder-Willi syndrome. In one embodiment, the carbetocin drug product is administered to the subject intranasally. In at least one embodiment, a total daily dose of carbetocin is from about 1 mg/day to about 30 mg/day. In at least one embodiment, a total daily dose of carbetocin is from about 8.0 mg/day to about 30.0 mg/day. In at least one embodiment, a total daily dose of carbetocin is from about 9.0 mg/day to about 29.0 mg/day. In one embodiment, a total daily dose of carbetocin is chosen from about 8.0 mg/day, about 9.0 mg/day, 10.0 mg/day, about 11.0 mg/day, about 12.0 mg/day, about 13.0 mg/day, about 14.0 mg/day, 15.0 mg/day. 16.0 mg/day, 17.0 mg/day, 18.0 mg/day, 19.0 mg/day, 20.0 mg/day, 21.0 mg/day, 22.0 mg/day, 23.0 mg/day, 24.0 mg/day, 25.0 mg/day, 26.0 mg/day, 27.0 mg/day, 28.0 mg/day, 29.0 mg/day, and about 30.0 mg/day. In another embodiment, a total daily dose of carbetocin is chosen from about 9.1 mg/day, about 9.2 mg/day, about 9.3 mg/day, about 9.4 mg/day, about 9.5 mg/day, about 9.6 mg/day, about 9.7 mg/day, about 9.8 mg/day, and about 9.9 mg/day. In at least one embodiment, a total daily dose of carbetocin is 9.6 mg/day. In one embodiment, a total daily dose of carbetocin is chosen from about 11.1 mg/day, about 11.2 mg/day, about 11.3 mg/day, about 11.4 mg/day, about 11.5 mg/day, about 11.6 mg/day, about 11.7 mg/day, about 11.8 mg/day, and about 11.9 mg/day. In at least one embodiment, a total daily dose of carbetocin is 11.4 mg/day. In one embodiment, a total daily dose of carbetocin is chosen from about 28.1 mg/day, about 28.2 mg/day, about 28.3 mg/day, about 28.4 mg/day, about 28.5 mg/day, about 28.6 mg/day, about 28.7 mg/day, about 28.8 mg/day, and about 28.9 mg/day. In at least one embodiment, a total daily dose of carbetocin is 28.8 mg/day. In at least one embodiment, the total daily dose is divided into 3 equal doses. In another embodiment, the carbetocin drug products disclosed show improved stability and bioavailability. In at least some embodiments, the pharmaceutical preparation is an aqueous solution of about 10 mg/mL to about 70 mg/mL carbetocin that includes a hydrotrope and a viscoelastic polymer in such concentrations that the solution retains 75-125% of the bioavailability (as measured by the area under the curve and the maximum concentration) of an aqueous solution of carbetocin in saline.

In some embodiments, the carbetocin drug products are administered intranasally daily for a period of time. In at least one embodiment, the carbetocin drug products are administered intranasally up to 3 times daily for chronic use. In at least one embodiment, the carbetocin drug product is administered in a volume of about 50 µL to about 200 µL into one nostril and then a volume of about 50 µL to about 200 µL into the second nostril, for a combined volume of about 100 µL to about 400 µL for both nostrils. In at least one embodiment, the carbetocin drug products are administered intranasally 3 times daily for 20 consecutive days. In at least one embodiment, the carbetocin drug product is administered in a volume of about 20 µL to about 200 µL into one nostril and then a volume of about 20 µL to about 200 µL into the second nostril, for a combined volume of about 40 µL to about 400 µL for both nostrils. In at least one embodiment, the carbetocin drug product is administered in a volume of about 25 µL to about 35 µL into one nostril and then a volume of about 25 µL to about 35 µL into the second nostril, for a combined volume of about 50 µL to about 70 µL for both nostrils. In one embodiment, the carbetocin drug product is administered in a volume of 140 µL into one nostril and then a volume of 140 µL into the second nostril, for a combined volume of 280 µL for both nostrils. In some embodiments, the administered dose of carbetocin remains uniform (i.e., consistent) over a period of time.

In another aspect, the disclosure provides a method of administering carbetocin to a subject diagnosed with Präder-Willi syndrome, wherein two or three doses per day of 3.2 mg/dose carbetocin are administered intranasally to the patient. According to this aspect, the disclosure provides a method of administering carbetocin to a subject diagnosed with PrAder-Willi syndrome, wherein three doses per day of 3.2 mg/dose carbetocin are administered intranasally to the patient. The disclosure also provides a method of administering carbetocin to a subject diagnosed with PrAder-Willi syndrome, wherein each dose is administered within 30 minutes of a meal or just before a meal. In another aspect, the disclosure provides a method of administering carbetocin to a subject diagnosed with Präder-Willi syndrome, wherein carbetocin is administered for at least one week, at least two weeks, at least three weeks, at least four weeks, at least one month, at least two months, at least three months, or longer.

The disclosure also provides a method of administering carbetocin to a subject diagnosed with Präder-Willi syndrome, wherein the administration results in one or more of (a) decrease in hyperphagia behavior compared to placebo, optionally as measured by the Hyperphagia Questionnaire for Clinical Trials (HQ-CT) Total Score; (b) decrease in obsessive and compulsive behavior compared to placebo, optionally as measured by the Children's Yale-Brown Obsessive-Compulsive Scale (CY-BOCS) Total Score; (c) decrease in anxiety compared to placebo, optionally as measured by the PWS Anxiety and Distress Questionnaire (PADO) Total Score; and (d) improvement in global clinical impression compared to placebo, optionally as measured by the Clinical Global Impression of Change (CGI-C) score. According to this aspect, the disclosure provides a method of administering carbetocin to a subject diagnosed with Präder-Willi syndrome, wherein the administration results in a decrease in hyperphagia behavior. According to this aspect, the disclosure provides a method of administering carbetocin to a subject diagnosed with Präder-Willi syndrome, wherein the administration results in a decrease in hyperphagia behavior and a decrease in obsessive and compulsive behavior.

In another aspect, the disclosure provides a method of administering carbetocin to a subject diagnosed with Präder-Willi syndrome, wherein the age of the subject is from seven (7) to eighteen (18) years old, inclusive. According to this aspect, the disclosure provides a method of administering carbetocin to a subject diagnosed with Prader-Willi syndrome, wherein the subject is aged seven (7) years old, eight (8) years old, nine (9) years old, ten (10) years old, eleven

(11) years old, twelve (12) years old, thirteen (13) years old, fourteen (14) years old, fifteen (15) years old, sixteen (16) years old, seventeen (17) years old, or eighteen (18) years old.

BRIEF DESCRIPTION OF DRAWINGS

The foregoing summary, as well as the following detailed description of the disclosure, will be better understood when read in conjunction with the appended drawings. For the purpose of illustrating the present disclosure, the attached drawings illustrate some, but not all, alternative embodiments. It should be understood, however, that the disclosure is not limited to the precise arrangements and instrumentalities shown. These figures, which are incorporated into and constitute part of the specification, assist in explaining the principles of the disclosure.

DETAILED DESCRIPTION OF THE DISCLOSURE

Figure 1:
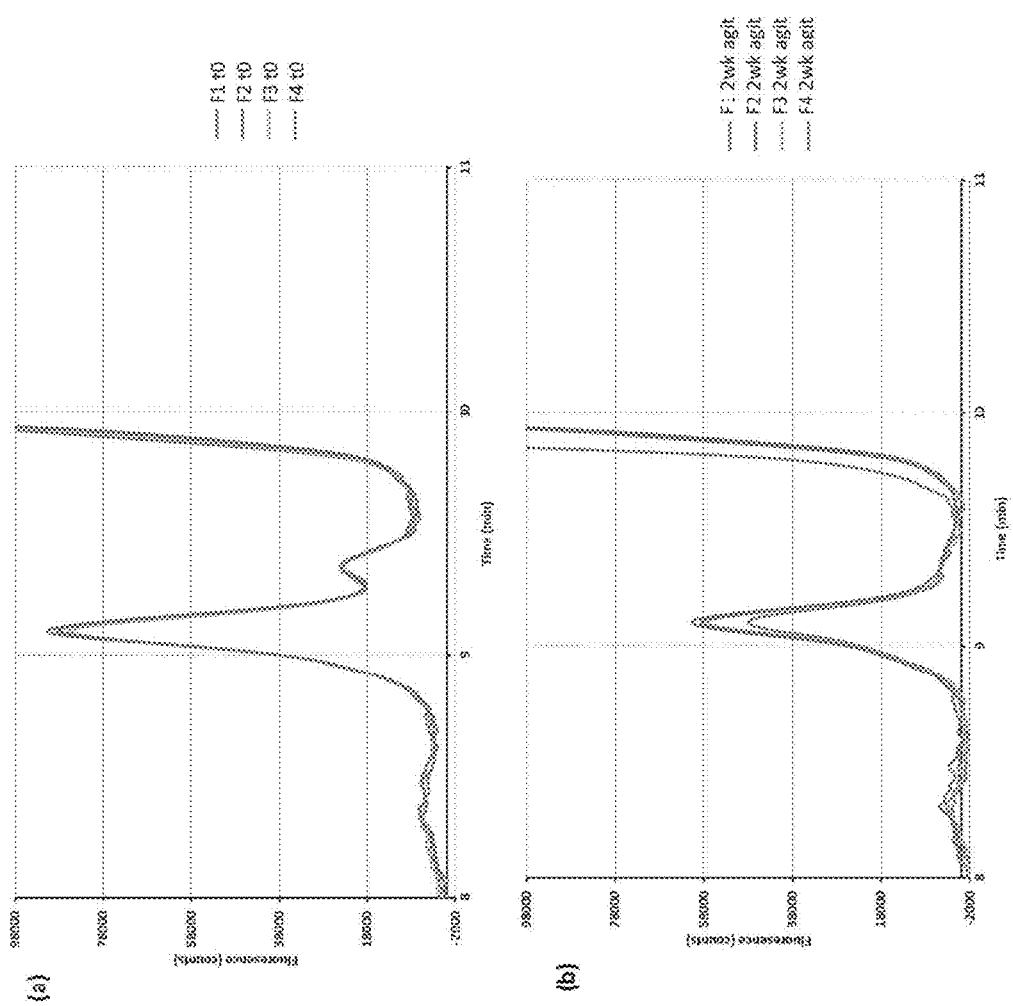
FIG. 1. shows a visual depiction of the loss of the high molecular weight (HMW) content in the filtered/agitated samples. (a) Expanded view of high molecular weight species from SEC for HPMC formulations at time-zero. (b) Expanded view of HMW species from SEC for HPMC formulations that were re-filtered and agitated for 14 days at room temperature.

It should be understood that both the foregoing general description and the following detailed description are exemplary and explanatory but are not restrictive of the invention as claimed. Certain details of one or more embodiments of the invention are set forth in the description below. Those of skill in the art will recognize that there are numerous variations and modifications of the invention that are encompassed by its scope. Other features or advantages of the present disclosure will be apparent from the representative examples that follow, and also from the appending claims.

The present disclosure provides an improved process to make a carbetocin drug product. The carbetocin drug product (pharmaceutical preparation) comprises an aqueous solution of carbetocin and a pharmaceutically acceptable excipient, including but not limited to the following excipients: hydrotropes, tonicity enhancers, and/or surface active agents, such as a viscoelastic polymer, for example, HPMC, and combinations thereof. The carbetocin drug products disclosed may include but do not require a surfactant. The carbetocin drug products of the present disclosure exhibit improved stability despite their relatively high concentrations of carbetocin. For example, in certain embodiments, the method provides improved carbetocin drug products that are free from aggregate-forming solids and that show little to no visible solids after extended periods of time at room temperature. In other embodiments, the carbetocin drug products of the present disclosure exhibit little to no visible solids after shaking stress. The carbetocin drug products disclosed herein may be formulated in a container having reduced headspace, which may include close to or substantially zero headspace to minimize the gas-water interface. In certain embodiments, however, it is unnecessary to reduce headspace to maintain improved stability. The carbetocin drug products disclosed exhibit improved stability despite their relatively high concentrations of carbetocin (e.g., 210 mg/mL). Certain embodiments are stable under conditions of stress, such as mechanical stress (e.g., shaking and stirring, pumping, freeze-thaw processes). The carbetocin drug products of the present disclosure also possess advantageously extended in-use time and/or shelf life for the patient. For example, the carbetocin drug product of the present disclosure exhibits an in-use time ranging from 1 day to 7 days, and includes embodiments wherein the content uniformity of carbetocin remains consistent and high throughout the in-use period. In some embodiments, the carbetocin drug product of the present disclosure also possess good local tolerability after 14 days at room temperature. In at least some embodiments, the carbetocin drug product of the present disclosure possess good local tolerability after 3-7 days at room temperature.

In one embodiment, the process of making a carbetocin drug product comprises at least one polar solvent in the processing, formulation, and manufacturing of the carbetocin drug product. In some embodiments, the at least one polar solvent can be, but is not limited to, water (H—OH). In at least some embodiments, the water is chosen from water for injection ("WFI"), highly purified water ("HPW"), and purified water. In another embodiment, other polar solvents may be optionally added to the preparation. In some embodiments, the other polar solvents can be, but are not limited to, acetic acid ($CH_3CO$—OH), methanol ($CH_3$—OH), n-propanol ($CH_3CH_2CH_2$—OH), and n-butanol ($CH_3CH_2CH_2CH_2$—OH). In at least one embodiment, the present disclosure is directed to a process of making a carbetocin drug product comprising an aqueous solution of carbetocin and a hydrotrope and/or HPMC, wherein the concentration of carbetocin ranges from about 1 mg/mL to about 50 mg/mL.

For example, the concentration of carbetocin ranges from 1 mg/mL to 70 mg/mL, such as from 5 to 55 mg/mL, from 10 mg/mL to 50 mg/mL, from 15 mg/mL to 35 mg/mL, or from 30 mg/mL to 34 mg/mL. In at least one embodiment, the concentration of carbetocin in solution is about 40 mg/mL. In another embodiment, the concentration of carbetocin ranges from about 15 mg/mL to about 45 mg/mL. In at least one embodiment, the concentration of carbetocin ranges from about 10 mg/mL to about 40 mg/mL. In at least one embodiment, the concentration of carbetocin may be, for example, about 11 mg/mL, about 15 mg/mL, about 20 mg/mL, about 25 mg/mL, about 30 mg/mL, about 33 mg/mL, about 34 mg/mL, about 35 mg/mL, 36 mg/mL, about 37 mg/mL, about 38 mg/mL, about 39 mg/mL, or about 40 mg/mL. In at least one embodiment, the concentration of carbetocin may be, for example, about 1 mg/mL, about 2 mg/mL, about 3 mg/mL, about 4 mg/mL, about 8 mg/mL, about 11.4 mg/mL, about 20 mg/mL, or about 34.3 mg/mL. In another embodiment, the concentration of carbetocin may be, for example, 34.1 mg/mL, 34.2 mg/mL, 34.3 mg/mL, 34.4 mg/mL, 34.5 mg/mL, 34.6 mg/mL, 34.7 mg/mL, 34.8 mg/mL, 34.9 mg/mL, or 40 mg/mL. In one embodiment, the concentration of carbetocin is about 34.3 mg/mL.

For the carbetocin drug products of the present disclosure one or more of cyclodextrin, amino acid, hydrotrope and/or hydroxypropyl methylcellulose (HPMC) is included in the carbetocin drug product disclosed. In at least one embodiment, the method of making the carbetocin drug product comprises at least one hydrotrope. Examples of hydrotropes include but are not limited to aromatic anionic compounds, aromatic cationic compounds, or aliphatic, linear compounds. In some embodiments, the aromatic anionic compound is chosen from sodium benzoate, sodium salicylate, sodium benzene sulfonate, sodium benzene disulfonate, sodium cinnamate, sodium 3-hydroxy-2-naphthoate, sodium para-toluene sulfonate, sodium cumene sulfonate, nicotinamide, N,N-diethylnicotinamide, or N,N-dimethyl benzamide. In one embodiment, the hydrotrope is nicotinamide.

In some embodiments, the aromatic cationic compound is chosen from para-aminobenzoic acid hydrochloride, procaine hydrochloride, or caffeine. In other embodiments, the aliphatic, linear compound is chosen from sodium alkanoate, urea, or N,N-dimethyl urea.

In at least one embodiment, the hydrotrope is selected from the group consisting of nicotinamide, sodium benzoate, and salicylate salts (e.g., sodium salicylate, potassium salicylate, lithium salicylate, ammonium salicylate, calcium salicylate, and magnesium salicylate).

If present in the carbetocin drug product, the amino acid may be chosen from a natural or unnatural amino acid. In one embodiment, the natural amino acid is arginine. In at least some embodiments, the unnatural amino acids may be chosen from f-amino acids, homo-amino acids, proline and pyruvic acid derivatives, 3-substituted alanine derivatives, glycine derivatives, ring-substituted phenylalanine and tyrosine derivatives, linear core amino acids, or N-methyl amino acids. In some embodiments, the unnatural amino acid is an arginine derivative chosen from L-2-amino-3-guanidinopropionic acid hydrochloride and 4-guanidinobutyric acid.

If present in the carbetocin drug product, the solubilizer may be chosen from a cyclodextrin derivative. In at least some embodiments, the cyclodextrin derivative is chosen from methyl-β-cyclodextrin, randomly methylated-β-cyclodextrin (RM-β-CD), sulfobutylether-β-cyclodextrin (SBE-β-CD), epichlorohydrin-β-cyclodextrin, and carboxy methyl epichlorohydrin beta cyclodextrin. In some embodiments, the cyclodextrin derivative is methyl-p-cyclodextrin.

If present in the carbetocin drug product, the surface active agent may be chosen from a cellulose derivative. In at least one embodiment, the cellulose derivative may be chosen from hydroxypropyl cellulose (HPC), hydroxypropyl methylcellulose (HPMC), and carboxy methyl ethyl cellulose (CMEC). In some embodiments, the cellulose derivative is HPMC.

In at least some embodiments, the hydrotrope is present in a concentration ranging from 50 mM to 500 mM. In at least some embodiments, the hydrotrope is present in a concentration ranging from 100 mM to 400 mM. In at least one embodiment, the hydrotrope concentration ranges from about 200 mM to about 300 mM, such as from 200 mM to 220 mM, from 240 mM to 260 mM, or from 280 mM to 300 mM. In at least one embodiment, the concentration of the hydrotrope is about 400 mM. In at least one embodiment, the concentration of the hydrotrope is about 300 mM. In another embodiment, the concentration of the hydrotrope is about 200 mM.

If present in the process of making the carbetocin drug product, nicotinamide is present in a concentration ranging from 50 mM to 500 mM. In at least one embodiment, the nicotinamide concentration ranges from about 200 mM to about 350 mM, such as from 200 mM to 220 mM, from 240 mM to 260 mM, from 280 mM to 300 mM, or from 320 mM to 340 mM. In at least one embodiment, the concentration of nicotinamide is, for example, about 200 mM, about 210 mM, about 220 mM, about 230 mM, about 240 mM, about 250 mM, about 260 mM, about 270 mM, about 280 mM, about 290 mM, about 300 mM, about 310 mM, about 320 mM, about 330 mM, about 340 mM, about 350 mM, about 360 mM, about 370 mM, about 380 mM, about 290 mM, or about 400 mM. In at least one embodiment, the concentration of nicotinamide is about 400 mM. In at least one embodiment, the concentration of nicotinamide is about 350 mM. In at least one embodiment, the concentration of nicotinamide is about 300 mM. In at least one embodiment, the concentration of nicotinamide is about 250 mM. In another embodiment, the concentration of nicotinamide is about 200 mM.

In at least some embodiments, HPMC is present in the carbetocin drug product in an amount ranging from 0.005% to 0.05% w/v. In at least one embodiment, HPMC is present in an amount ranging from 0.0075% to 0.0125% w/v. In another embodiment, HPMC is present in an amount ranging from 0.0075% to 0.01% w/v. In at least one embodiment, HPMC is present in an amount of 0.01% w/v. In at least one embodiment, the grade of HPMC is chosen from low viscosity (e.g., 10-20 cP), medium viscosity (e.g., 40-60 cP), and high viscosity (e.g., 80-120 cP, 4000 cP). In at least one embodiment, HPMC is high viscosity grade. In at least one embodiment, the high viscosity HPMC possesses a viscosity of 4000 cP.

In at least some embodiments, the addition of HPMC to the carbetocin drug product reduces aggregation of an aqueous solution of carbetocin compared to an aqueous solution of carbetocin that does not contain HPMC, including embodiments wherein the carbetocin aqueous solution is aggregated to form aggregation-forming solids and thereafter filtered to remove said aggregate-forming solids. In some embodiments, the aggregation of the carbetocin solution is reduced by at least 20% and up to 50% when compared to an aqueous solution of carbetocin that does not contain HPMC. In other embodiments, the aggregation of the carbetocin solution is reduced by at least 20% compared to an aqueous solution of carbetocin that does not contain HPMC. In some embodiments, the aggregation of the carbetocin solution is reduced by at least 30% compared to an aqueous solution of carbetocin that does not contain HPMC. In some embodiments, the aggregation of the carbetocin solution is reduced by at least 40% compared to an aqueous solution of carbetocin that does not contain HPMC. In some embodiments, the aggregation of the carbetocin solution is reduced by at least 50% compared to an aqueous solution of carbetocin that does not contain HPMC.

In some embodiments, the process of making an improved carbetocin drug product may optionally contain an additional excipient. Non-limiting examples of additional excipients include sorbitol, ethylenediaminetetraacetic acid (EDTA), potassium sorbate, mannitol, and sodium or potassium acetate. These additional excipients may be included even if only a hydrotrope or HPMC is present alone in the carbetocin drug product. For example, the pharmaceutical preparation contains at least one hydrotrope and/or HPMC with at least one additional excipient.

A tonicity enhancer/modifier (exicipient) may be, but is not required, to provide isotonic formulations (e.g., 300 mOsm/Kg). In at least one embodiment, the osmolality of a carbetocin drug product is preferably adjusted to maximize the carbetocin's stability and/or to minimize discomfort to the patient upon administration. In at least one embodiment, the carbetocin drug product for direct administration to a patient is isotonic, which may be achieved by addition of a tonicity modifier, such as sorbitol. Other non-limiting examples of tonicity modifiers include amino acids (e.g., cysteine, arginine, histidine, glycine etc.), salts (e.g., sodium chloride, potassium chloride, sodium citrate etc.) or non-electrolytes (e.g., sugars or polyols, such as, for example, sucrose, glucose and mannitol).

In some embodiments, the process of making an improved carbetocin drug product measures the viscosity values before and after agitation of the carbetocin solution. In at least some embodiments, between pre-agitation/filtration to T=0 (i.e., post-agitation/filtration $T_0$—HPLC) there may be a decrease in viscosity for some preparations that may be associated with the filtration step. In other embodiments, the carbetocin preparations that have the highest HPMC concentration do not show a decrease in viscosity between pre-agitation/filtration to T=0. In another embodiment, the carbetocin preparations show a slight decrease in viscosity. In other embodiments, there is an increase in viscosity for some preparations between T=0 and T=24 hours that may be associated with aggregation/formation of particulates. In some embodiments, the smallest increase in viscosity from T=0 to T=24 hours may be 1.14 cP to 1.23 cP. In other embodiments, the highest increase in viscosity from T=0 to T=24 hours may be 0.64 cP to 1.36 cP. In some embodiments, the average pre-agitation/filtration sample viscosity may be 1.24 cP.

In some embodiments, the process of making an improved carbetocin drug product measures the osmolality values before and after agitation. In one embodiment, the process of making carbetocin has no significant effect on the final osmolality values of the carbetocin preparations as compared to the pre-agitation/filtration solutions comprising carbetocin. In some embodiments the preparations containing a lower carbetocin concentration have lower osmolality values.

If present in the carbetocin drug product of the present disclosure, the excipient is added to adjust the osmolality to, for example, about 225 mOsm/Kg, about 226 mOsm/Kg, about 227 mOsm/Kg, about 228 mOsm/Kg, about 229 mOsm/Kg, about 230 mOsm/Kg, about 231 mOsm/Kg, about 232 mOsm/Kg, about 233 mOsm/Kg, about 234 mOsm/Kg, about 235 mOsm/Kg, about 236 mOsm/Kg, about 237 mOsm/Kg, about 238 mOsm/Kg, about 239 mOsm/Kg, about 240 mOsm/Kg, about 241 mOsm/Kg, about 242 mOsm/Kg, about 243 mOsm/Kg, about 244 mOsm/Kg, about 245 mOsm/Kg, about 246 mOsm/Kg, about 247 mOsm/Kg, about 248 mOsm/Kg, about 249 mOsm/Kg, about 250 mOsm/Kg, about 251 mOsm/Kg, about 252 mOsm/Kg, about 253 mOsm/Kg, about 254 mOsm/Kg, about 255 mOsm/Kg, about 256 mOsm/Kg, about 257 mOsm/Kg, about 258 mOsm/Kg, about 259 mOsm/Kg, about 260 mOsm/Kg, about 261 mOsm/Kg, about 262 mOsm/Kg, about 263 mOsm/Kg, about 264 mOsm/Kg, about 265 mOsm/Kg, about 266 mOsm/Kg, about 267 mOsm/Kg, about 268 mOsm/Kg, about 269 mOsm/Kg, about 270 mOsm/Kg, about 271 mOsm/Kg, about 272 mOsm/Kg, about 273 mOsm/Kg, about 274 mOsm/Kg, about 275 mOsm/Kg, about 276 mOsm/Kg, about 277 mOsm/Kg, about 278 mOsm/Kg, about 279 mOsm/Kg, about 280 mOsm/Kg, about 281 mOsm/Kg, about 282 mOsm/Kg, about 283 mOsm/Kg, about 284 mOsm/Kg, about 285 mOsm/Kg, about 286 mOsm/Kg, about 287 mOsm/Kg, about 288 mOsm/Kg, about 289 mOsm/Kg, about 290 mOsm/Kg, about 291 mOsm/Kg, about 292 mOsm/Kg, about 293 mOsm/Kg, about 294 mOsm/Kg, about 295 mOsm/Kg, about 296 mOsm/Kg, about 297 mOsm/Kg, about 298 mOsm/Kg, about 299 mOsm/Kg, about 300 mOsm/Kg, about 310 mOsm/Kg, about 320 mOsm/Kg, about 330 mOsm/Kg, about 340 mOsm/Kg, about 350 mOsm/Kg, about 360 mOsm/Kg, about 370 mOsm/Kg, about 380 mOsm/Kg, about 390 mOsm/Kg, about 400 mOsm/Kg, about 410 mOsm/Kg, about 420 mOsm/Kg, about 430 mOsm/Kg, about 440 mOsm/Kg, about 450 mOsm/Kg, about 460 mOsm/Kg, about 470 mOsm/Kg, about 480 mOsm/Kg, about 490 mOsm/Kg, about 500 mOsm/Kg, about 510 mOsm/Kg, about 520 mOsm/Kg, about 530 mOsm/Kg, about 540 mOsm/Kg, about 550 mOsm/Kg, about 560 mOsm/Kg, about 570 mOsm/Kg, about 580 mOsm/Kg, about 600 mOsm/Kg, about 610 mOsm/Kg, about 620 mOsm/Kg, about 630 mOsm/Kg, about 640 mOsm/Kg, about 650 mOsm/Kg, about 660 mOsm/Kg, about 670 mOsm/Kg, about 680 mOsm/Kg, about 700 mOsm/Kg, about 710 mOsm/Kg, about 720 mOsm/Kg, about 730 mOsm/Kg, about 740 mOsm/Kg, about 750 mOsm/Kg, about 760 mOsm/Kg, about 770 mOsm/Kg, about 780 mOsm/Kg, or about 800 mOsm/Kg. In some embodiments, the osmolality may be in excess of 800 mOsm/Kg. In at least one embodiment, the osmolality is about 290 mOsm/Kg. In at least one embodiment, the excipient is sorbitol.

In some embodiments, sorbitol is present in a concentration ranging from 100 mM to 300 mM. In some embodiments, sorbitol is present in a concentration ranging from 110 mM to 287 mM. In some embodiments, sorbitol is added to adjust the osmolality to, for example, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM, about 190 mM, about 195 mM, about 200 mM, 205 mM, about 210 mM, about 215 mM, about 220 mM, about 225 mM, about 230 mM, 235 mM, about 240 mM, about 245 mM, about 250 mM, about 255 mM, about 260 mM, 265 mM, about 270 mM, about 275 mM, about 280 mM, about 285 mM, about 290 mM, or about 300 mM. In at least one embodiment, the concentration of sorbitol is chosen from about 110 mM, about 120 mM, about 150 mM, about 200 mM, about 250 mM, or about 287 mM. In at least one embodiment, the concentration of sorbitol is about 110 mM. In at least one embodiment, the concentration of sorbitol is about 130 mM.

In at least one embodiment, the hydrotrope is nicotinimide. In some embodiments, the nicotinimide is present in the carbetocin drug product in a concentration ranging from 50 mM to 500 mM. In at least one embodiment, the nicotinimide concentration ranges from about 100 mM to about 350 mM, such as from 150 mM to 220 mM, from 240 mM to 280 mM, or from 300 mM to 350 mM. In at least one embodiment, the concentration of nicotinimide is about 200 mM. In at least one embodiment, the concentration of nicotinamide is about 300 mM. In at least one embodiment, the concentration of nicotinimide is about 400 mM.

The disclosed method of making a carbetocin drug product may comprise an aqueous solution of carbetocin and solubilizer and/or surface active agent chosen from a hydrotrope, cyclodextrin, amino acid, and/or HPMC in a container, wherein the headspace in the container is near zero (i.e., limited headspace). In another embodiment, such a pharmaceutical preparation with reduced headspace does not include a surfactant. That is, the present disclosure of making an improved carbetocin drug product includes a pharmaceutical preparation comprising an aqueous solution of carbetocin and a hydrotrope, cyclodextrin, amino acid, and/or HPMC in a container, wherein the headspace in the container is near zero, and wherein the preparation is substantially free of a surfactant (e.g., non-ionic surfactant n-dodecyl-3-D-maltoside (DDM), Tween 20 or 80), for example, such that the carbetocin drug product does not include a surfactant. In at least one embodiment, a surface active agent is not present in the carbetocin drug product disclosed.

The term "headspace" is a term well understood in the art and refers to gas space within a sealed container containing a solution. The volume of the headspace may vary depending on the entire inner volume of the container and the amount of solution it contains. For example, in at least one embodiment, the headspace represents about 2.0 mL, 1.9 mL, 1.8 mL, 1.7 mL, 1.6 mL, 1.5 mL, 1.4 mL, 1.3 mL, 1.2 mL, 1.1 mL, 1.0 mL, 0.9 mL, about 0.8 mL, about 0.7 mL, about 0.6 mL, about 0.5 mL, about 0.4 mL, about 0.3 mL, about 0.2 mL, about 0.18 mL, about 0.15 mL, about 0.12 mL, about 0.1 mL, about 0.08 mL, about 0.07 mL, about 0.06 mL, about 0.05 mL, about 0.04 mL, about 0.03 mL, about 0.020 mL, or about 0.01 mL of the volume of the container comprising the carbetocin solution. In at least one embodiment, the headspace represents about 80%, about 70%, about 60%, about 50%, about 45%, about 40%, about 35%, about 30%, about 25%, about 20%, about 15%, about 12%, about 10%, about 9%, about 8%, about 7%, about 6%, about 5%, about 4%, about 3%, about 2%, about 1.5%, about 1%, about 0.75%, about 0.5%, about 0.25%, or about 0.1% of the volume of the container comprising the carbetocin solution. In at least one embodiment, the headspace represents less than 0.5%, less than 0.4%, less than 0.3%, less than 0.2%, less than 0.1%, less than 0.001%, or 0.0% of the total volume of the container. In at least one embodiment of the present disclosure, the container headspace is substantially zero. As used herein, the term "route of administration" may include, but is not limited to, oral, rectal, buccal, nasal, vaginal, transdermal (e.g. patch technology); parenteral, intravenous, intramuscular or subcutaneous injection; intracisternal, intravaginal, intraperitoneal, local (powders, ointments or drops) or as a buccal or nasal spray. The drug product may be an injectable composition or injectable formulation. Injectable formulations can be supplied in any suitable container, e.g. ampoule, vial, pre-filled syringe, injection device, injection cartridge, ampoule, (multi-) dose pen and the like. The drug product may be used for intra-muscular administration (e.g. intramuscular injection) or intravenous administration (e.g. IV injection). In some embodiments, the intranasal preparations of the disclosure are administered using any spray bottle or syringe. For example, a nasal spray may be administered by a nasal spray pump, which delivers a volume of 140 µL into one nostril and then a volume of 140 µL into the second nostril, for a combined volume of 280 µL for both nostrils. In at least some embodiments, the amount of carbetocin in solution delivered by spray does not decrease over time.

The carbetocin drug products disclosed are advantageous because the carbetocin drug products are stable even at high concentrations of carbetocin, such as at a concentration ranging from about 11 mg/mL to about 70 mg/mL, including about 34 mg/mL.

In at least one embodiment, the stability of the carbetocin drug product is evident because it resists aggregate formation, and the aqueous solution has little to no visible solids (e.g., particles). In at least some embodiments, the carbetocin drug product of the disclosed process has no visible aggregate-forming solids under accelerated conditions of stress. In at least some embodiments, the carbetocin drug product has no aggregate-forming solids, such as, for example, large snowflakes like clumps, small flakes, large flakes and gel on glass, small clumps, layer of clumps at meniscus forming raft, complete raft at meniscus, specs, small specs, webby aggregates at meniscus, or particulates. In some embodiments, the carbetocin drug product exhibits no visible solids when inspected visually after a period of 24 hours after continuous shaking.

In some embodiments, the carbetocin in solution has little to no visible solids when stored at room temperature (~25° C.) for a sustained period of time. In some embodiments, the carbetocin drug product disclosed is not prone to aggregation for long periods of time. For example, in some embodiments, the carbetocin solution has little to no visible solids for up to 5 years. In some embodiments, the carbetocin solution has little to no visible solids for up to 4 years. In some embodiments, the carbetocin solution has little to no visible solids for up to 3 years. In some embodiments, the concentration of carbetocin in the aqueous solution does not change over time (e.g., over 3, 4, or 5 years).

In at least one embodiment, a stable aqueous solution of carbetocin is a solution meeting the U.S. Pharmacopeial Convention (USP) reference standard 787 titled "Subvisible Particulate Matter In Therapeutic Protein Injections." Exemplary cut-offs include: if the container volume is <100 mL, the solution has less than 6000 particles/container >10 micrometer (µm) in size and 600 particles/container >25 µm in size; and if the container volume is >100 mL; the solution has less than 25 particles/mL >10 µm in size and 3 particles/mL>25 µm in size.

In at least one embodiment, the post-agitation carbetocin drug product has before (the second) agitation at time 0 hours (i.e., T=0 hours) less than about 800 sub-visible particles ≥1 µm-<2 µm in size per 2 milliliter of solution. In another embodiment, a stable aqueous solution of carbetocin is a solution having less than about 222 sub-visible particles ≥2 µm-<10 µm in size per 2 milliliter of solution. In another embodiment, a stable aqueous solution of carbetocin is a solution having less than about 4 sub-visible particles ≥10 µm-<25 µm in size per 2 milliliter of solution. In another embodiment, a stable aqueous solution of carbetocin is a solution having less than about 7 sub-visible particles ≥25 µm in size per 2 milliliter of solution.

In at least one embodiment, the post-agitation carbetocin drug product has after the second agitation at time 24 hours (i.e., T=24 hours) less than about 8850 sub-visible particles ≥1 µm-<2 µm in size per 2 milliliter of solution. In another embodiment, a stable aqueous solution of carbetocin is a solution having less than about 2826 sub-visible particles ≥2 μm-<10 μm in size per 2 milliliter of solution. In another embodiment, a stable aqueous solution of carbetocin is a solution having less than about 69 sub-visible particles ≥10 μm-<25 μm in size per 2 milliliter of solution. In another embodiment, a stable aqueous solution of carbetocin is a solution having less than about 14 sub-visible particles ≥25 μm in size per 2 milliliter of solution.

In at least one embodiment, the post-agitation carbetocin drug product has before (the second) agitation at time 0 hours (i.e., T=0 hours) less than about 941 sub-visible particles ≥1 μm-<2 μm in size per 2 milliliter of solution. In another embodiment, a stable aqueous solution of carbetocin is a solution having less than about 381 sub-visible particles ≥2 μm-<10 μm in size per 2 milliliter of solution. In another embodiment, a stable aqueous solution of carbetocin is a solution having less than about 28 sub-visible particles ≥10 μm-<25 μm in size per 2 milliliter of solution. In another embodiment, a stable aqueous solution of carbetocin is a solution having less than about 14 sub-visible particles ≥25 μm in size per 2 milliliter of solution.

In at least one embodiment, the post-agitation carbetocin drug product has after the second agitation at time 24 hours (i.e., T=24 hours) less than about 7118 sub-visible particles ≥1 μm-<2 μm in size per 2 milliliter of solution. In another embodiment, a stable aqueous solution of carbetocin is a solution having less than about 4768 sub-visible particles ≥2 μm-<10 μm in size per 2 milliliter of solution. In another embodiment, a stable aqueous solution of carbetocin is a solution having less than about 626 sub-visible particles ≥10 μm-<25 μm in size per 2 milliliter of solution. In another embodiment, a stable aqueous solution of carbetocin is a solution having less than about 211 sub-visible particles ≥25 μm in size per 2 milliliter of solution.

In at least one embodiment, the post-agitation carbetocin drug product has before (the second) agitation at time 0 hours (i.e., T=0 hours) less than about 2565 sub-visible particles ≥1 μm-<2 μm in size per 2 milliliter of solution. In another embodiment, a stable aqueous solution of carbetocin is a solution having less than about 581 sub-visible particles ≥2 μm-<10 μm in size per 2 milliliter of solution. In another embodiment, a stable aqueous solution of carbetocin is a solution having less than about 17 sub-visible particles 10 μm-<25 μm in size per 2 milliliter of solution. In another embodiment, a stable aqueous solution of carbetocin is a solution having less than about 6 sub-visible particles ≥25 μm in size per 2 milliliter of solution.

In at least one embodiment, the post-agitation carbetocin drug product has after the second agitation at time 24 hours (i.e., T=24 hours) less than about 54435 sub-visible particles ≥1 μm-<2 μm in size per 2 milliliter of solution. In another embodiment, a stable aqueous solution of carbetocin is a solution having less than about 13984 sub-visible particles ≥2 μm-<10 μm in size per 2 milliliter of solution. In another embodiment, a stable aqueous solution of carbetocin is a solution having less than about 463 sub-visible particles ≥10 μm-<25 μm in size per 2 milliliter of solution. In another embodiment, a stable aqueous solution of carbetocin is a solution having less than about 152 sub-visible particles ≥25 μm in size per 2 milliliter of solution.

In some embodiments, the carbetocin drug products comprise HPMC. In at least some embodiments, the carbetocin drug products containing low viscosity grade HPMC show higher particle counts for particles over 10 μm at T=24 hours when compared to preparations containing high viscosity grade HPMC. In one embodiment, aggregation is reduced as the carbetocin concentration decreases.

In other embodiments, the carbetocin drug products containing low viscosity grade HPMC may form a high number of small particles (≥10 μm), for example, when the HPMC concentration is increased above 0.01% w/v. In some embodiments, there may also be an increase in the number of large particles (≥10 μm) from concentrations of 0.02% w/v for 40-60 cP HPMC. In other embodiments, the large particle count decreases to a minimum at HPMC concentration 0.0075% w/v for 4000 cP HPMC. In other embodiments, preparations with more than 0.0075% w/v HPMC may show a slight increase in the large particle count with increasing concentration of HPMC before peaking at 0.0125% w/v.

In at least some embodiments, the carbetocin drug products made using the disclosed process contain a high viscosity grade HPMC. In some embodiments, the carbetocin drug products comprising high viscosity HPMC generally form fewer large particles than those containing the low viscosity grade HPMC. In one embodiment, the ratio of HPMC to carbetocin may be more sensitive with 40-60 cP HPMC than it is with 4000 cP HPMC. In some embodiments, an HPMC concentration ranging from about 0.0075% to about 0.01% w/v is used in the carbetocin drug products disclosed herein.

In at least some embodiments, the carbetocin drug products show no visible aggregate after 24 hours of shaking stress. Thus, the pharmaceutical preparations of the present disclosure remain stable to shaking stress. For example, the aqueous carbetocin solution is stable to shaking stress for a period of time. In some embodiments, the carbetocin drug product is subjected to shaking stress for 24 hours at 25° C., and the aqueous carbetocin solution is substantially free of the aggregate-forming solids. In some embodiments, the carbetocin drug product is subjected to shaking stress for 3, 6, 12, and 24 hours at 25° C., and the aqueous carbetocin solution remains clear with little to no visible particles. In at least one embodiment, the carbetocin drug products are stable to shaking stress for at least 1 hour, 2 hours, 3 hours, 4 hours, 5 hours, 6 hours, 7 hours, 8 hours, 9 hours, 10 hour, 11 hours, 12 hours, 13 hours, 14 hours, 15 hours, 16 hours, 17 hours, 18 hours, 19 hours, 20 hours, 21 hours, 22 hours, 23 hours, or 24 hours, and the aqueous carbetocin solution remains clear with little to no visible particles.

The stability of the carbetocin drug products may also be measured by the chromatographic purity of carbetocin. In at least one embodiment, controls at one or more days assure that chromatographic purity of carbetocin is greater than 95%. In at least one embodiment, controls at one or more days assure that chromatographic purity of carbetocin is greater than 96%. In at least one embodiment, controls at one or more days assure that chromatographic purity of carbetocin is greater than 97%. In at least one embodiment, the chromatographic purity of carbetocin is greater than 98%. In at least one embodiment, the chromatographic purity of carbetocin is greater than 99%. In at least one embodiment, the chromatographic purity of carbetocin is greater than 99.4%. In at least one embodiment, the chromatographic purity of carbetocin is greater than 99.5%. In at least one embodiment, the chromatographic purity of carbetocin is greater than 99.6%. In at least one embodiment, the chromatographic purity of carbetocin is greater than 99.7%. In at least one embodiment, the chromatographic purity of carbetocin is greater than 99.8%. In at least one embodiment, the chromatographic purity of carbetocin is greater than 99.9%. In at least one embodiment, carbetocin is not subject to chemical degradation, i.e., there is minimal or no change in chromatographic purity of carbetocin before or after shaking stress. In addition, the pharmaceutical preparations of the present disclosure exhibit stability in that the concentration of carbetocin in solution does not change over time, including under conditions of shaking stress.

In at least one embodiment, the chromatographic purity of carbetocin in solution with the excipients disclosed is greater than 98% after 24 hours of stress. In at least one embodiment, the chromatographic purity of carbetocin in solution with the excipients disclosed is greater than 98% after 36 hours of stress. In at least one embodiment, the chromatographic purity of carbetocin in solution with the excipients disclosed is greater than 98% at 48 hours of stress. In at least one embodiment, the chromatographic purity of carbetocin in solution with the excipients disclosed is greater than 98% at 72 hours of stress.

In at least one embodiment, the chromatographic purity of carbetocin in solution with the excipients disclosed is greater than 99% after 24 hours of stress. In at least one embodiment, the chromatographic purity of carbetocin in solution with the excipients disclosed is greater than 99.5% after 24 hours of stress.

In general, the carbetocin drug product of the present disclosure will have a pH from about 3.0 to about 6.3. In at least one embodiment, the pH of the aqueous carbetocin solution may be from 3.5 to 5.9, for example from 5.35 to 5.7, or for example from 5.3 to 5.4. In some embodiments of the present disclosure, the pH of the carbetocin drug product is from about 5.3 to about 5.5; about 5.3±3; 5.4±3; or 5.5±3. In at least one embodiment, the pH of the aqueous carbetocin solution is 5.4±0.5. In another embodiment, the pH of the aqueous carbetocin solution is 5.4±0.3. In another embodiment, the pH of the aqueous carbetocin solution is 5.4±0.1.

In some embodiments, the pH may vary throughout the process of making an improved carbetocin drug product. For example, between pre-agitation/filtration (i.e., pre-agitation preparation) to T=0 (i.e., post-agitation carbetocin drug product) there may be either a slight decrease in pH or it may remain constant. In some embodiments, between T=0 and T=24 hours there may be a significant pH increase in the preparations. For example, as the concentration of carbetocin decreases the initial pH increases. In some embodiments, the preparations have a pH in the range of 3.0-6.26 throughout the disclosed process. In one embodiment, the pH of the final solution is not significantly affected by, for example, the HPMC concentration. In other embodiments, there is no significant difference in the grade of HPMC used in relation to final pH in solution The carbetocin drug products of the present disclosure include a container. For example, suitable containers comprise a recipient part connected to an opening and a closing means. In at least one embodiment, the container consists of a recipient part connected to an opening and a closing means such as a regular pharmaceutically acceptable vial fitted with a closing cap, prefilled syringes, capsules or ampoules. In at least one embodiment, the container is a regular pharmaceutically acceptable vial fitted with a closing cap. The container can be fitted with hermetically closing means such as a cap hermetically closing the vial and protecting the aqueous protein solution from the surrounding outside atmosphere. In at least some embodiments, the container may be chosen from an ampoule, vial, pre-filled syringe, injection device, injection cartridge, ampoule, (multi-) dose pen and the like. In another embodiment, the container may be chosen from a glass beaker, volumetric flask, an ampoule, vial, or pre-filled filed intranasal dispenser. In at least one embodiment, the container is an ampoule or a vial. In at least one embodiment, the container is a vial. In some embodiments, the vial is a scintillation vial.

In some embodiments, the carbetocin drug product disclosed herein has the following properties:
  (a) no visible aggregate-forming solids made by visual assessment, which may include via photographs;
  (b) a low particle count for particles over 10 μm for 34.3 mg/mL carbetocin formulations in MFI;
  (c) meets pH specification for pre-filter/agitation at all time points evaluated during the disclosed process; and
  (d) viscosity result below average (e.g., 34.3 mg/mL carbetocin formulations at T=24 (1.23 cP, avg=1.31 cP)).

In at least some embodiments, the present disclosure provides a method of making an improved carbetocin drug product comprising an aqueous solution of carbetocin and a solubilizer and/or surface active agent, such as HPMC, wherein the carbetocin drug product shows a surprising content uniformity of carbetocin for long periods of time even after multiple freeze/thaw cycles. For example, the disclosed carbetocin drug products show content uniformity of carbetocin after one or more freeze/thaw cycles for a duration chosen from 1 day, 2 days, 3 days, 4 days, 5 days, 6 days, and 7 days. In at least some embodiments, the carbetocin drug product has little to no aggregate-forming solids by visual assessment after thawing for 3-7 days. In some embodiments, the carbetocin in the disclosed carbetocin drug product is evenly distributed throughout the carbetocin drug product to ensure that if the carbetocin drug product is, for example, split in one or more preparations, each resulting preparation has an equal dose of carbetocin. In one embodiment, the disclosed carbetocin drug products have a consistent (i.e., uniform) dose of carbetocin, which is maintained between various preparation batches so that the patient/subject receives the correct dose. In at least one embodiment, the disclosed carbetocin drug product provides enhanced convenience and patient compliance. In some embodiments, the consistent dose of carbetocin varies by no more than 20% between various preparation batches. In some embodiments, the consistent dose of carbetocin varies by no more than 15% between various preparation batches. In some embodiments, the consistent dose of carbetocin varies by no more than 10% between various preparation batches. In some embodiments, the consistent dose of carbetocin varies by no more than 5% between various preparation batches. In some embodiments, the consistent dose of carbetocin varies by no more than 2.5% between various preparation batches.

Methods of Preparation

In at least one embodiment, the present disclosure provides a method of making an improved carbetocin drug product, including those free of visible particles, such as aggregate-forming solids. In at least one embodiment, a carbetocin drug product of aqueous carbetocin is prepared, for example, in a container. In at least one embodiment, the disclosure provides a method for preparing a carbetocin drug product of aqueous carbetocin and a container, wherein the concentration of carbetocin ranges from about 1 mg/mL to about 70 mg/mL, comprising:
  (a) agitating an aqueous solution comprising carbetocin and one or more excipients;
  (b) allowing aggregate-forming solids to form; and
  (c) removing the formed aggregate-forming solids,
  wherein the carbetocin drug product is substantially free of the aggregate-forming solids. In at least one embodiment, the one or more excipients are chosen from surface active agents, solubilizers, and combinations thereof. In some embodiments, the one or more excipients are chosen from a hydrotrope, a cyclodextrin, an amino acid, a cellulose derivatives, and combinations thereof.

In at least one embodiment, the method comprises:
(a) adding water to a container and stirring the water preparation;
(b) adding at least one solubilizer and/or surface active agent to the preparation of step (a) and optionally adding one or more excipients to the preparation to adjust osmolality;
(c) adding carbetocin to the preparation of step (b) until carbetocin is completely dissolved in solution and optionally adjusting the solution to a target volume with water, and further filtering the solution to obtain a pre-agitation preparation, wherein the solution has a pH ranging from about 3.0 to about 6.26.
(d) agitating the preparation from step (c) for a period of time to induce aggregate-forming solids to formand filtering off the aggregate-forming solids from the carbetocin preparation; and
(e) saving the filtrate that is free of the aggregate-forming solids in a container to obtain a post-agitation carbetocin drug product, wherein the carbetocin drug product is substantially free of the aggregate-forming solids.

In at least one embodiment, the carbetocin drug product is substantially free of the aggregate-forming solids.

In at least one embodiment, the method further comprises a step in which the post-agitation carbetocin drug product is further agitated for another 24 hours. In some embodiments, the post-agitation carbetocin drug product takes more time to aggregate compared to a pre-agitation carbetocin preparation. In at least some embodiments, the post-agitation carbetocin drug product is stable to aggregation under accelerated conditions of stress for extended periods of time. In some embodiments, the post-agitation carbetocin drug product is stable to aggregation under accelerated conditions of stress for at least 24 hours.

In at least one embodiment, an aliquot (e.g., 1 mL) is taken for HPLC analysis in step (c) after the filtering of the solution. The aliquot is labelled "pre-agitation/filtration—HPLC". The pre-agitation preparations are also assessed for pH, osmolality and viscosity before step (d).

In at least one embodiment, the carbetocin preparation is agitated in step (d) by magnetic stirring at, for example, 200 rpm for 24 hours. Then, in step (d), an aggregate is observed after the carbetocin preparation is agitated for a period of time. In at least some embodiments, the period of time may be chosen from 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, or 48 hours. In at least one embodiment, the period of time is 24 hours.

In some embodiments, the aggregate-forming solids may be in the form of, for example, small clumps, small flakes, specks, large flakes, gel or gel on glass, and particulates.

In some embodiments, after the filtrate is saved/transferred in, for example, a dry scintillation vial in step (e), an aliquot (e.g., 1 mL) is taken from the filtrate for HPLC analysis and is labelled "post-agitation/filtration $T_0$—HPLC." The filtrates are then assessed for pH, osmolality, viscosity and by MFI. In one embodiment, sub-visible particles are evaluated using the MFI Model Protein simple. In one embodiment, the viscosity is evaluated using a Viscosity meter Model DV-II+Pro. In one embodiment, shaking stress is induced using a Shaker Model Heidolph, Titramax 1000. In at least some embodiments, the post-agitation carbetocin drug product from step (e) is a clear solution, free from visible particulates. In at least some embodiments, the carbetocin drug product is substantially free of the aggregate-forming solids. In some embodiments, the aggregate-forming solids are filtered off via a syringe filter. In one embodiment, the syringe filter is a 0.22 µm, Polyethersulfone (PES) syringe filter.

In some embodiments, the post-agitation carbetocin drug products from step (e) are further assessed for stability to shaking stress. In at least some embodiments, the filtrates from step (e) are added to dry vials and then placed in a box on a shaker and further agitated at 200 rpm for 24 hours. In one embodiment, photographs are taken of the vials at 3, 6, 12 and 24-hour time points. After 24 hours of agitation on, for example, a rocker, aliquots are taken for HPLC analysis and labelled "post-agitation/filtration $T_{24}$—HPLC." The post-agitation/filtration $T_{24}$ are also assessed for pH, osmolality, viscosity and by MFI.

In at least one embodiment, the method comprises:
(a) adding water to a container and stirring the water preparation;
(b) adding nicotinimide, HPMC, and optionally sorbitol to the preparation of step (a);
(c) adding carbetocin to the preparation of step (b) until carbetocin is completely dissolved in solution and optionally adjusting the solution to a target volume with water, and further filtering the solution to obtain a pre-agitation preparation, wherein the concentration of carbetocin ranges from about 1 mg/mL to about 70 mg/mL and the solution has a pH ranging from about 3.0 to about 6.3;
(d) agitating the preparation from step (c) for a period of time to induce aggregate-forming solids to formand filtering off the aggregate-forming solids from the carbetocin preparation; and
(e) saving the filtrate that is free of the aggregate-forming solids in a container to obtain a post-agitation carbetocin drug product, wherein the carbetocin drug product is substantially free of the aggregate-forming solids.

In at least one embodiment, the carbetocin drug product disclosed herein has little to no visible solids after shaking for 24 hours. In at least one embodiment, the carbetocin drug product disclosed herein has little to no visible solids after shaking for 48 hours. In at least one embodiment, the carbetocin drug product disclosed herein has little to no visible solids after shaking for 72 hours. In at least one embodiment, the carbetocin drug product disclosed herein has little to no visible solids after shaking for 96 hours. In at least one embodiment, carbetocin is not subject to chemical degradation before or after the shaking stress. In at least one embodiment, controls at one or more days assure that chromatographic purity of carbetocin is greater than 98%. In at least one embodiment, the chromatographic purity of carbetocin is greater than 99%. In at least one embodiment, the chromatographic purity of carbetocin is 99.4±0.0%. In at least one embodiment, the chromatographic purity of carbetocin is 99.4±0.1%. In at least one embodiment, the chromatographic purity of carbetocin is 99.4±0.2%. In at least one embodiment, the chromatographic purity of carbetocin is 99.5±0.0%. In at least one embodiment, the chromatographic purity of carbetocin is 99.5±0.1%. In at least one embodiment, the chromatographic purity of carbetocin is 99.5±0.2%. In at least one embodiment, the chromatographic purity of carbetocin is 99.8±0.3%. In at least one embodiment, the chromatographic purity of carbetocin is 99.9±0.1%.

Exemplary Pharmaceutical Preparations

In at least one embodiment, a carbetocin drug product comprises carbetocin and one or more excipients, and pharmaceutically acceptable salts thereof, wherein the carbetocin drug product is substantially free of the aggregate-forming solids.

In at least one embodiment, a carbetocin drug product comprises:
  (a) an aqueous solution of carbetocin, wherein the carbetocin is present in a concentration of about 1 mg/mL to about 70 mg/mL;
  (b) hydrotrope and/or HPMC; and
  (c) optionally an additional excipient, wherein the preparation has a pH ranging from about 3.0 to about 5.8, and wherein the carbetocin drug product is substantially free of the aggregate-forming solids.

In at least one embodiment, a carbetocin drug product comprises:
  (a) an aqueous solution of carbetocin, wherein the carbetocin is present in a concentration of about 1 mg/mL to about 70 mg/mL;
  (b) nicotinamide;
  (c) HPMC; and
  (d) sorbitol, wherein the solution has a pH ranging from about 3.0 to about 5.8.

In at least one embodiment, a carbetocin drug product comprises:
  (a) carbetocin, wherein the carbetocin is present in a concentration of about 25 mg/mL to about 35 mg/mL;
  (b) nicotinamide, wherein the nicotinamide is present in a concentration of about 200 mM;
  (c) HPMC, wherein the HPMC is present in an amount ranging from 0.0075% to 0.05% w/v; and
  (d) sorbitol, wherein the sorbitol is present in a concentration ranging from about 110 mM to about 150 mM.

In at least one embodiment, a carbetocin drug product comprises:
  (a) carbetocin, wherein the carbetocin is present in a concentration of about 34.3 mg/mL;
  (b) nicotinamide, wherein the nicotinamide is present in a concentration of about 200 mM;
  (c) HPMC, wherein the HPMC is present in an amount of about 0.01% w/v; and
  (d) sorbitol, wherein the sorbitol is present in a concentration ranging from about 100 mM to about 200 mM.

In at least one embodiment, a carbetocin drug product comprises:
  (a) carbetocin, wherein the carbetocin is present in a concentration of about 11.4 mg/mL;
  (b) nicotinamide, wherein the nicotinamide is present in a concentration of about 200 mM;
  (c) HPMC, wherein the HPMC is present in an amount of about 0.01% w/v; and
  (d) sorbitol, wherein the sorbitol is present in a concentration ranging from about 100 mM to about 200 mM.

In at least one embodiment, a carbetocin drug product comprises:
  (a) carbetocin, wherein the carbetocin is present in a concentration of about 1 mg/mL to about 4 mg/mL;
  (b) nicotinamide, wherein the nicotinamide is present in a concentration of about 200 mM;
  (c) HPMC, wherein the HPMC is present in an amount ranging from 0.0075% % to 0.01% w/v; and
  (d) sorbitol, wherein the sorbitol is present in a concentration ranging from about 100 mM to about 200 mM.

In at least one embodiment, a carbetocin drug product comprises:
  (a) carbetocin, wherein the carbetocin is present in a concentration of about 34.3 mg/mL;
  (b) nicotinamide, wherein the nicotinamide is present in a concentration of about 200 mM;
  (c) HPMC, wherein the HPMC is present in an amount of about 0.0075%; and
  (d) sorbitol, wherein the sorbitol is present in a concentration of about 110 mM.

In at least one embodiment, a carbetocin drug product comprises:
  (a) carbetocin, wherein the carbetocin is present in a concentration of about 34.3 mg/mL;
  (b) nicotinamide, wherein the nicotinamide is present in a concentration of about 200 mM;
  (c) HPMC, wherein the HPMC is present in an amount of about 0.01%; and
  (d) sorbitol, wherein the sorbitol is present in a concentration of about 110 mM.

In at least one embodiment, a carbetocin drug product comprises:
  (a) carbetocin, wherein the carbetocin is present in a concentration of about 11.4 mg/mL;
  (b) nicotinamide, wherein the nicotinamide is present in a concentration of about 200 mM;
  (c) HPMC, wherein the HPMC is present in an amount of about 0.01%; and
  (d) sorbitol, wherein the sorbitol is present in a concentration of about 110 mM to about 130 mM. The present disclosure also includes a stable intranasal pharmaceutical preparation comprising: an aqueous solution of carbetocin and one or more excipients, wherein the solution exhibits at least 10 to 50% longer time to appearance of visible solids when inspected visually after a period of time of continuous shaking stress while exposed to air at room temperature compared to a control solution (e.g., without excipients), and preferably wherein the stable intranasal pharmaceutical preparation has good local tolerability.

The present disclosure also includes a stable intranasal pharmaceutical preparation comprising: an aqueous solution of carbetocin and one or more excipients, wherein the solution exhibits at least 10 to 50% longer time to appearance of visible solids when inspected visually after a period of time chosen from 1 day, 2 days, 3 days, 4 days, 5 days, 6 days, or 7 days of continuous 200 rpm shaking stress with a 3 cm shaking amplitude while exposed to air at room temperature compared to a control solution (e.g., without excipients), and preferably wherein the disclosed intranasal pharmaceutical preparation has good local tolerability.

The present disclosure also includes a stable intranasal pharmaceutical preparation comprising:
  an aqueous solution of carbetocin and one or more excipients, wherein the solution has good local tolerability and where it resists aggregation as measured by various standard techniques, such as A350.

Also included is a stable intranasal pharmaceutical preparation comprising: an aqueous solution of carbetocin comprising a reduced amount of aggregate-forming solids compared to an aqueous solution of carbetocin that is not subject to an HPMC treatment, such as adding HPMC, agitating the solution to produce aggregate-forming solids, and filtering, wherein the reduced amount of aggregate-forming solids provides at least 20 to 50% longer time to appearance of visible solids when inspected visually after continuous 200 rpm shaking stress with a 3 cm shaking amplitude while exposed to air at room temperature compared to the aqueous solution of carbetocin that is not subject to an HPMC treatment. In each of these exemplary embodiments, the headspace of the container may optionally be reduced. In addition, the headspace may be substantially zero for each of these exemplary embodiments.

The carbetocin drug products disclosed herein may optionally include one or more pharmaceutically acceptable solvents. In at least one embodiment, the one or more solvents may be present as a mixture with water, such as, for example, a pharmaceutically acceptable alcohol and water.

The present disclosure also provides for a kit of parts comprising: a liquid (e.g., aqueous) carbetocin drug product comprising carbetocin with the excipients disclosed, wherein the pH of the composition is from 3.0 to 5.8; and a container for the composition, optionally with separate injection means (e.g., if required for administration), optionally with instructions for administration of the composition. The pH of the composition may be from 4.15 to 5.75, for example from 5.2 to 5.65. The pH of the composition may be from 5.30 to 5.8, for example from 5.40 to 5.70, for example from 5.50 to 5.6. In at least one embodiment, the pH of the composition is about 5.4. In at least one embodiment, the pH of the aqueous carbetocin solution is 5.4±0.5. In another embodiment, the pH of the aqueous carbetocin solution is 5.4±0.3. In another embodiment, the pH of the aqueous carbetocin solution is 5.4±0.1.

Methods of Treatment

In at least one embodiment, the disclosure provides a method of treating a subject suffering from, or susceptible to, a disease that is beneficially treated by a carbetocin drug product comprising the step of administering to said subject an effective amount of the carbetocin drug product disclosed herein.

In at least one embodiment, the improved carbetocin drug products may be for use in (or in the manufacture of medicaments for) the treatment or prevention of neurodevelopmental disorders, including Präder-Willi syndrome, in a mammalian subject in need thereof. In at least one embodiment, a therapeutically-effective amount of a pharmaceutical preparation of the present disclosure is administered to a subject suffering from PrAder-Willi syndrome.

In some embodiments, the disclosure provides a method of administering an aqueous solution of carbetocin intranasally comprising instructions for administration of the carbetocin drug product or pharmaceutical preparation over several days (e.g., 3-7 days).

EXAMPLES

The present disclosure may be better understood by reference to examples. The following examples are intended for illustration purposes only and should not be construed as limiting the scope of the disclosure in any way. Further, the section headings used herein are for organizational purposes only and are not to be construed as limiting the subject matter described.

Methods:

Visual Inspection

Storage stability and agitation samples were analyzed for particles in a light box against both a white and black background. Pictures were taken to document any particles/precipitate formed in these samples.

A350

Absorbance at 350 nm was monitored to track formation of large, soluble aggregates in storage stability and agitation samples. For these measurements, 300 µL of solution was measured in a reduced volume, 1 cm path-length quartz cuvette. MO water was used as the blank for all measurements. Note, A350 is a light scattering technique, so it is most effective for measuring scattering in solutions containing large, soluble aggregates, or solutions with a homogeneous dispersion of non-soluble particles.

Example 1

Carbetocin was obtained as a powder and was stored at s 20° C. until ready for use. Formulations were prepared by dissolving the desired amount of carbetocin in an aqueous solution containing the desired excipients, if any. The pH of each formulation was adjusted to the desired pH by addition of an appropriate amount of 5 M NaOH. All preparations were prepared using multi-compendial grade excipients and reagents, and ultra-pure water (Millipore MilliQ, 18MΩ). The osmolality of each preparation was measured before preparing the final formulation to ensure it was similar to that of the theoretically determined value. Each formulation (bulk material) was sterile filtered using a Millipore Millex-GV syringe filter (0.22 µm). 1.2 mL of each sterile filtered formulation was filled into a 3 mL glass vial, stoppered with a 13 mm Fluorotec coated serum stopper, and crimped. All materials (i.e., vials, stoppers, etc.) were sterilized before filling.

Lyophilization

Carbetocin was lyophilized with excipients. Table 1 lists the 4 formulations lyophilized. All formulations used in this study were first lyophilized using a Millrock Model RD85S3 Revo lyophilizer (Millrock Technologies, Kingston, NY). The general lyophilization procedure used for all cycles consisted of an initial cooling/freezing step, an annealing step (if there were crystallizable excipients present), a primary drying step, and a secondary drying step. A nitrogen back-fill (at 580 Torr) was employed at the end of each cycle, and all samples were stoppered under nitrogen before removing from the lyophilizer. The fill volume for the lyophilized formulations in the study was 1.2 mL into a 3 mL glass vial. Sterile filtering and aliquotting was conducted in a biosafety cabinet using materials (i.e., vials, stoppers, etc.) which had been previously sterilized.

The formulation design for the samples used in this study is summarized in Table 1 below.

TABLE 1

| Form | Carbetocin mg/mL | Acetate (mM) | Sorbitol (mM) | Arg HCl (mM) | Nicotinamide (mM) | EDTA (% w/v) | Sorbate* (% w/v) | HPMC (% w/v) |
|---|---|---|---|---|---|---|---|---|
| 1 | 35 | 7.4 | 0 | 0 | 0 | 0.1 | 0.12 | 0.05 |
| 2 | 35 | 50 | 200 | 0 | 0 | 0 | 0 | 0.05 |
| 3 | 35 | 7.4 | 0 | 0 | 200 | 0 | 0 | 0.01 |
| 1 | 35 | 7.4 | 0 | 50 | 200 | 0 | 0 | 0.01 |

*sorbate = potassium sorbate

Filtration and Re-agitation of HPMC samples

This study was performed to evaluate the effect of filtration and re-agitation of carbetocin samples comprising HPMC. First, formulations were prepared by reconstituting the lyo formulations shown in Table 1. The carbetocin concentration for all formulations was 35 mg/mL, and the pH was adjusted to 5.4±0.1. After sterile preparation, samples were placed horizontally on an orbital plate shaker (Labnet, 3 mm orbit) and shaken continuously at 200 rpm for a prescribed period of time (e.g., 28 h, 48 h). Samples were shielded from ambient light during agitation. All samples used in this study were agitated at room temperature. Then, the agitated/precipitated HPMC formulations (F1, F2, F3, F4) from the first agitation were filtered with a 0.22 μm PVDF filter (4 mm) and re-agitated. The results obtained for the non-agitated (time zero) and re-filtered HPMC samples are summarized in Tables 2-4 below.

TABLE 2

Carbetocin concentration (from RP-HPLC) for non-agitated (time-zero) and re-filtered HPMC samples agitated for 2 weeks

| Form | time-zero (mg/ml) | Post-Filtration 2 wks Agitation (mg/mL) |
|---|---|---|
| F1 | 36.0 | 38.1 |
| F2 | 37.9 | 38.9 |
| F3 | 36.6 | 37.7 |
| F4 | 37.4 | 38.2 |

TABLE 3

% Purity (from RP-HPLC) measured for non-agitated (time-zero), agitated non-filtered (pre-filtration), and filtered samples agitated for 2 weeks (post-filtration, 2 wks agitation)

| Form | Time-Zero | Pre-Filtration | Post-Filtration 2 wks Agitation |
|---|---|---|---|
| F1 | 99.49 | 99.51 | 99.47 |
| F2 | 99.51 | 99.52 | 99.54 |
| F3 | 99.50 | 99.50 | 99.51 |
| F4 | 99.51 | 99.52 | 99.49 |

TABLE 4

% Monomer (from SEC) and % high molecular weight (HMW) species measured for non-agitated (time-zero) and filtered samples agitated for 2 weeks (filtered w/2 wks agitation)

| Form | % Monomer Time-Zero | % Monomer Filtered w/2 wks Agitation | % HMW Time-Zero | % HMW Filtered w/2 wks Agitation |
|---|---|---|---|---|
| F1 | 99.86 | 99.91 | 0.12 | 0.07 |
| F2 | 99.87 | 99.91 | 0.13 | 0.09 |
| F3 | 99.87 | 99.91 | 0.13 | 0.09 |
| F4 | 99.87 | 99.92 | 0.13 | 0.08 |

Results

First, it was noticed that formulations 1 and 2 (see Table 1) containing 0.05% (w/v) HPMC were more difficult to filter (required multiple filters) than those containing 0.01% (w/v) HPMC (required a single filter; see formulations 3 and 4).

Second, re-agitation of the filtered material resulted in samples that were much more resistant to agitation induced precipitation than the original samples. It was observed that only after 3 days of continuous agitation was any precipitate evident in these samples (F1, F2), and even then its presence was hard to discern. Additional agitation for up to 14 days resulted in visible precipitate in all samples, but the amount was far less than that seen in the original agitation samples. Content determination by RP-HPLC indicated that the amount of carbetocin lost during precipitation was negligible and not quantifiable using this method. The RP-HPLC result was verified by A280 content measurements made on applicable samples (those without nicotinamide; absorb at 280 nm). Purity measurements obtained from RP-HPLC (see Tables 2 and 3) indicated that the agitated material did not undergo chemical degradation during agitation. It was noted that the SEC measurements (see Table 4) made on the filtered/agitated samples revealed that the high molecular weight (HMW) content was somewhat diminished vs. t0 after 2 wks of agitation. This result suggested that HMW material was potentially being lost during agitation. A visual depiction of this loss is given in the SEC chromatograms in FIGS. 1a and 1b, which compares the HMW region pre and post-agitation (2 wks).

Example 2

Aggregation of Carbetocin, Effect of Shaking Stress

To study the aggregation process, various concentrations of carbetocin were chosen and prepared using the disclosed process which is detailed below.

Preparation of Stock Solutions

Stock Solution A

Preparation of 0.5% (w/v) HPMC 4000 cP 2.5 g of HPMC (4000 cP) was weighed into a weighing boat. Approximately 400 mL WFI was added into a 1 L glass beaker containing a magnetic stirrer bar. The HPMC was added slowly with stirring to the WFI. The beaker was covered with aluminium foil and heated to 60° C. for 3 hours with constant stirring, before the heater was switched off and the solution was left to stir overnight to allow complete dissolution. The solution was then transferred to a 500 cm3 volumetric flask and made up to target volume with WFI.

Stock Solution B

Preparation of 0.5% (w/v) HPMC 40-60 cP 2.5 g of HPMC (4000 cP) was weighed into a weighing boat. Approximately 400 mL WFI was added into a 1 L glass beaker containing a magnetic stirrer bar. The HPMC was added slowly with stirring to the WFI. The beaker was covered with aluminium foil and heated to 60° C. for 3 hours with constant stirring, before the heater was switched off and the solution was left to stir overnight to allow complete dissolution. The solution was then transferred to a 500 $cm^3$ volumetric flask and made up to target volume with WFI.

Stock Solution C

Preparation of 2M Nicotinamide 245 g of nicotinamide was weighed into a glass beaker. Approximately 400 mL WFI was added into a 2 L glass beaker containing a magnetic stirrer bar. The nicotinamide was added slowly with stirring to the WFI until complete dissolution. The solution was then transferred to a 1000 $cm^3$ volumetric flask and made up to target volume with WFI.

Stock Solution D

Preparation of 1.1 M Sorbitol 100.2 g of sorbitol was weighed into a glass beaker. Approximately 400 mL WFI was added into a 1 L glass beaker containing a magnetic stirrer bar. The sorbitol was added slowly with stirring to the WFI until complete dissolution. The solution was then transferred to a 1000 $cm^3$ volumetric flask and made up to target volume with WFI.

Stock solutions A, B, C and D were used to prepare the experiments outlined in Table 5. For each solution, carbetocin was weighed out and the appropriate volume of stock solutions added and made to final volume with WFI. Table 6 shows the testing matrix used to evaluate the formulations developed and Table 7 shows the appropriate volumes and weights of carbetocin.

TABLE 5

List of Experiments

| Experiment # | [Carbetocin] (mg) | [Nicotinamide] (mM) | [HPMC] (% w/v), Grade (cP) | [Sorbitol] (mM) | WFI |
|---|---|---|---|---|---|
| 1 | 34.3 | 200 | 0.0050, 4000 | 110 | To 1 mL |
| 2 | 34.3 | 200 | 0.0075, 4000 | 110 | To 1 mL |
| 3 | 34.3 | 200 | 0.0100, 4000 | 110 | To 1 mL |
| 4 | 34.3 | 200 | 0.0125, 4000 | 110 | To 1 mL |
| 5 | 34.3 | 200 | 0.0150, 4000 | 110 | To 1 mL |
| 6 | 34.3 | 200 | 0.0200, 4000 | 110 | To 1 mL |
| 7 | 34.3 | 200 | 0.0500, 4000 | 110 | To 1 mL |
| 8 | 34.3 | 200 | 0.0050, 40-60 | 110 | To 1 mL |
| 9 | 34.3 | 200 | 0.0075, 40-60 | 110 | To 1 mL |
| 10 | 34.3 | 200 | 0.0100, 40-60 | 110 | To 1 mL |
| 11 | 34.3 | 200 | 0.0125, 40-60 | 110 | To 1 mL |
| 12 | 34.3 | 200 | 0.0150, 40-60 | 110 | To 1 mL |
| 13 | 34.3 | 200 | 0.0200, 40-60 | 110 | To 1 mL |
| 14 | 34.3 | 200 | 0.0500, 40-60 | 110 | To 1 mL |
| 15 | 34.3 | 200 | 0.01, 4000 | 110 | To 1 mL |
| 16 | 20.0 | 200 | 0.01, 4000 | 110 | To 1 mL |
| 17 | 11.4 | 200 | 0.01, 4000 | 110 | To 1 mL |
| 18 | 8.0 | 200 | 0.01, 4000 | 110 | To 1 mL |
| 19 | 4.0 | 200 | 0.01, 4000 | 110 | To 1 mL |
| 20 | 3.0 | 200 | 0.01, 4000 | 110 | To 1 mL |
| 21 | 2.0 | 200 | 0.01, 4000 | 110 | To 1 mL |
| 22 | 1.0 | 200 | 0.01, 4000 | 110 | To 1 mL |

TABLE 6

Testing matrix

| | $T_0$ | $T_{3hrs}$ | $T_{6hrs}$ | $T_{12hrs}$ | $T_{24hrs}$ | $T_\infty$ |
|---|---|---|---|---|---|---|
| Appearance | ✓ | ✓ | ✓ | ✓ | ✓ | ✓ |
| Photograph | ✓ | ✓ | ✓ | ✓ | ✓ | ✓ |
| Osmolality | ✓ | | | | ✓ | ✓ |
| pH | ✓ | | | | ✓ | ✓ |
| MFI | ✓ | | | | ✓ | ✓ |
| Viscosity | ✓ | | | | ✓ | ✓ |
| HPLC | ✓ | | | | ✓ | ✓ |

TABLE 7

Weights and volumes

| Experiment # | Carbetocin weight (mg) | Volume, 2M Nicotinamide (mL) | Final [Nicotinamide] (mM) | Volume, 0.5% (w/v) HPMC solution (ml) | Final [HPMC] (% w/v), Grade (cP) | Volume, 1.1M Sorbitol (mL) | Final [Sorbitol] (mM) | WFI |
|---|---|---|---|---|---|---|---|---|
| 1 | 343 | 0.5 | 200 | 0.10 | 0.0050, 4000 | 1 | 110 | To 10 mL |
| 2 | 343 | 0.5 | 200 | 0.15 | 0.0075, 4000 | 1 | 110 | To 10 mL |
| 3 | 343 | 0.5 | 200 | 0.20 | 0.0100, 4000 | 1 | 110 | To 10 mL |
| 4 | 343 | 0.5 | 200 | 0.25 | 0.0125, 4000 | 1 | 110 | To 10 mL |
| 5 | 343 | 0.5 | 200 | 0.30 | 0.0150, 4000 | 1 | 110 | To 10 mL |
| 6 | 343 | 0.5 | 200 | 0.40 | 0.0200, 4000 | 1 | 110 | To 10 mL |
| 7 | 343 | 0.5 | 200 | 1.00 | 0.0500, 4000 | 1 | 110 | To 10 mL |
| 8 | 343 | 0.5 | 200 | 0.10 | 0.0050, 40-60 | 1 | 110 | To 10 mL |
| 9 | 343 | 0.5 | 200 | 0.15 | 0.0075, 40-60 | 1 | 110 | To 10 mL |
| 10 | 343 | 0.5 | 200 | 0.20 | 0.0100, 40-60 | 1 | 110 | To 10 mL |
| 11 | 343 | 0.5 | 200 | 0.25 | 0.0125, 40-60 | 1 | 110 | To 10 mL |
| 12 | 343 | 0.5 | 200 | 0.30 | 0.0150, 40-60 | 1 | 110 | To 10 mL |
| 13 | 343 | 0.5 | 200 | 0.40 | 0.0200, 40-60 | 1 | 110 | To 10 mL |
| 14 | 343 | 0.5 | 200 | 1.00 | 0.0500, 40-60 | 1 | 110 | To 10 mL |
| 15 | 343 | 0.5 | 200 | 0.20 | 0.01, 4000 | 1 | 110 | To 10 mL |
| 16 | 200 | 0.5 | 200 | 0.20 | 0.01, 4000 | 1 | 110 | To 10 mL |
| 17 | 114 | 0.5 | 200 | 0.20 | 0.01, 4000 | 1 | 110 | To 10 mL |
| 18 | 80 | 0.5 | 200 | 0.20 | 0.01, 4000 | 1 | 110 | To 10 mL |
| 19 | 40 | 0.5 | 200 | 0.20 | 0.01, 4000 | 1 | 110 | To 10 mL |
| 20 | 30 | 0.5 | 200 | 0.20 | 0.01, 4000 | 1 | 110 | To 10 mL |
| 21 | 20 | 0.5 | 200 | 0.20 | 0.01, 4000 | 1 | 110 | To 10 mL |
| 22 | 10 | 0.5 | 200 | 0.20 | 0.01, 4000 | 1 | 110 | To 10 mL |

Preparation method for Formulations 1-22

The appropriate weight of carbetocin was weighed into a weighing boat. Approximately 4 mL WFI was added into a 20 mL scintillation vial containing a magnetic stirrer bar. The appropriate volumes of excipients were added using a pipette. Carbetocin was added slowly with stirring to the solution until completely dissolved. The solution was then transferred to a 10 cm$^3$ volumetric flask and made up to target volume with WFI, before being transferred back into the scintillation vial. The solution was then filtered through a 0.22 μm, PES syringe filter. At this point a 1 mL aliquot was taken for HPLC analysis and labelled "pre-agitation/filtration—HPLC". The formulations were also assessed for pH, osmolality and viscosity.

The solutions remaining in the scintillation vials were then agitated by magnetic stirring at 200 rpm for 24 hours and filtered into clean, dry scintillation vials. A 1 mL aliquot was taken from the filtrate for HPLC analysis and labelled "post-agitation/filtration $T_0$—HPLC". The filtrates were assessed for pH, osmolality, viscosity and by MFI. A 2 mL sample of each filtrate was pipetted into 5 mL vials, which were stoppered and crimped. A photograph was taken of each vial for assessment of appearance at $T_0$.

The vials were then placed in a box on the shaker and agitated at 200 rpm for 24 hours. Photographs were taken of the vials at 3, 6, 12, and 24 hour time points. After 24 hours of agitation on the rocker, aliquots were taken for HPLC analysis and labelled "post-agitation/filtration $T_{24}$—HPLC". The formulations were also assessed for pH, osmolality, viscosity and by MFI. The results are summarized in Tables 8-15 below and FIGS. 2-11.

Results and Discussion

TABLE 8 pH results

| Experiment | Pre-Agitation/Filtration | Post-Filter $T_0$ | $T_{24}$ |
|---|---|---|---|
| 1 | 5.37 | 5.37 | 5.61 |
| 2 | 5.39 | 5.37 | 5.54 |
| 3 | 5.39 | 5.38 | 5.49 |
| 4 | 5.39 | 5.39 | 5.52 |
| 5 | 5.37 | 5.36 | 5.55 |
| 6 | 5.36 | 5.31 | 5.50 |
| 7 | 5.36 | 5.34 | 5.51 |
| 8 | 5.38 | 5.38 | 5.58 |
| 9 | 5.34 | 5.34 | 5.48 |
| 10 | 5.36 | 5.33 | 5.47 |
| 11 | 5.36 | 5.35 | 5.44 |
| 12 | 5.32 | 5.35 | 5.46 |
| 13 | 5.28 | 5.33 | 5.44 |
| 14 | 5.27 | 5.35 | 5.45 |
| 15 | 5.26 | 5.37 | 5.46 |
| 16 | 5.52 | 5.58 | 5.62 |
| 17 | 5.78 | 5.78 | 5.86 |
| 18 | 5.94 | 5.85 | 5.94 |
| 19 | 6.07 | 5.97 | 5.92 |
| 20 | 6.11 | 6.02 | 6.07 |
| 21 | 6.16 | 6.02 | 6.07 |
| 22 | 6.26 | 6.14 | 6.21 |

As can be seen from Table 8, the pH of the formulations was first studied. It was found that between pre-agitation/filtration to T=0 there was either a slight decrease in pH or it remained constant. It was further found that between T=0 and T=24 hours there was a significant pH increase in the majority of formulations (with exception of F19). The results from Table 8 show that as the concentration of carbetocin decreased the initial pH increased. It was noted that all formulations were in the range of 5.31-6.26 throughout the experiment (high of 5.61 at 34.3 mg/mL carbetocin).

The data shows that the pH of final solution was not significantly affected by the HPMC concentration (F1-7). It was noted that the largest increase after 24 hours was formulation 1 which had the least % of HPMC. There appeared to be no significant difference in the grade of HPMC used in relation to final pH in solution (F3 Vs F10) had pH values of 5.29 pH and 5.36, respectively when first prepared.

TABLE 9

Osmolality results

| Experiment | Pre-Agitation/Filtration (mOs/kg) | Post Filter $T_0$ (mOs/kg) | $T_{24/\infty}$ (mOs/kg) |
|---|---|---|---|
| 1 | 226 | 228 | 226 |
| 2 | 227 | 225 | 225 |
| 3 | 225 | 228 | 227 |
| 4 | 224 | 226 | 225 |
| 5 | 220 | 223 | 221 |
| 6 | 226 | 228 | 227 |
| 7 | 224 | 225 | 226 |
| 8* | 175 | 178 | 178 |
| 9 | 227 | 226 | 228 |
| 10 | 222 | 223 | 225 |
| 11 | 225 | 228 | 229 |
| 12 | No result | 228 | 229 |
| 13 | No result | 227 | 227 |
| 14 | No result | 229 | 229 |
| 15 | No result | 231 | 229 |
| 16 | No result | 214 | 213 |
| 17 | No result | 209 | 208 |
| 18 | No result | 204 | 204 |
| 19 | No result | 204 | 205 |
| 20 | No result | 205 | 205 |
| 21 | No result | 199 | 200 |
| 22 | No result | 197 | 198 |

*Formulation 8 from the osmolality value appeared to have been made incorrectly, so the results can be disregarded As can be seen from Table 9, the processing had no significant effect on the final osmolality values. It was also found that the formulations containing a lower carbetocin concentration had lower osmolality values. The osmolality values ranged from 197 to 231 mOsm/Kg. For example, formulations with 34.3 mg/mL carbetocin ranged from 221 mOsm/kg to 231 mOsm/kg. In addition, a formulation for, for example, intranasal administration would require an adjustment of sorbitol concentration or the addition of another tonicity enhancer to adjust the osmolality to approximately 290 mOsm/kg.

TABLE 10

Viscosity Results, Formulations 1-22

| Formulation | Time point | Viscosity (cP) | Torque (%) |
|---|---|---|---|
| 1 | T = pre-agitation | 1.37 | 89.3 |
|   | T = 0 | 1.14 | 74.1 |
|   | T = 24 hours | 1.23 | 80.4 |
| 2 | T = pre-agitation | 1.28 | 83.3 |
|   | T = 0 | 1.07 | 69.8 |
|   | T = 24 hours | 1.23 | 80.7 |
| 3 | T = pre-agitation | 1.27 | 82.8 |
|   | T = 0 | 1.32 | 86 |
|   | T = 24 hours | N/A | N/A |
| 4 | T = pre-agitation | 1.19 | 77.9 |
|   | T = 0 | 0.64 | 41.8 |
|   | T = 24 hours | 1.36 | 88.5 |
| 5 | T = pre-agitation | 1.25 | 81.3 |
|   | T = 0 | 0.79 | 51.5 |
|   | T = 24 hours | 1.28 | 83.8 |

TABLE 10-continued

Viscosity Results, Formulations 1-22

| Formulation Time point | | Viscosity (cP) | Torque (%) |
|---|---|---|---|
| 6 | T = pre-agitation | 1.13 | 73.7 |
|   | T = 0 | 0.96 | 62.9 |
|   | T = 24 hours | 1.51 | 98.9 |
| 7 | T = pre-agitation | 1.20 | 78.6 |
|   | T = 0 | 1.04 | 68 |
|   | T = 24 hours | N/A | N/A |
| 8 | T = pre-agitation | 0.83 | 54.2 |
|   | T = 0 | 0.52 | 33.6 |
|   | T = 24 hours | 1.29 | 84.3 |
| 9 | T = pre-agitation | 0.91 | 59.1 |
|   | T = 0 | 0.68 | 44.7 |
|   | T = 24 hours | N/A | N/A |
| 10 | T = pre-agitation | 0.93 | 60.7 |
|    | T = 0 | 0.55 | 35.3 |
|    | T = 24 hours | 1.27 | 83 |
| 11 | T = pre-agitation | 1.00 | 65.2 |
|    | T = 0 | 0.73 | 47.6 |
|    | T = 24 hours | 1.4 | 91.3 |
| 12 | T = pre-agitation | 1.27 | 83.1 |
|    | T = 0 | 0.68 | 44.2 |
|    | T = 24 hours | 1.13 | 73.6 |
| 13 | T = pre-agitation | 1.1 | 72.1 |
|    | T = 0 | 1.18 | 77.2 |
|    | T = 24 hours | 1.29 | 84.4 |
| 14 | T = pre-agitation | 1.1 | 72.1 |
|    | T = 0 | 1.32 | 85.8 |
|    | T = 24 hours | 1.23 | 80.3 |
| 15 | T = pre-agitation | 1.31 | 85.6 |
|    | T = 0 | 1.32 | 86.2 |
|    | T = 24 hours | *1.55 | 75.7 |
| 16 | T = pre-agitation | 1.22 | 79.6 |
|    | T = 0 | 1.25 | 81.5 |
|    | T = 24 hours | 1.11 | 72.7 |
| 17 | T = pre-agitation | 1.24 | 81 |
|    | T = 0 | 1.27 | 82.6 |
|    | T = 24 hours | 1.29 | 84.3 |
| 18 | T = pre-agitation | 1.14 | 74.6 |
|    | T = 0 | 1.29 | 84.4 |
|    | T = 24 hours | N/A | N/A |
| 19 | T = pre-agitation | 1.18 | 77.1 |
|    | T = 0 | 1.06 | 69.1 |
|    | T = 24 hours | 1.3 | 84.9 |
| 20 | T = pre-agitation | 1.16 | 75.5 |
|    | T = 0 | 1.32 | 85.9 |
|    | T = 24 hours | 1.24 | 80.9 |
| 21 | T = pre-agitation | 1.23 | 80.5 |
|    | T = 0 | 1.31 | 85.7 |
|    | T = 24 hours | 1.32 | 86.2 |
| 22 | T = pre-agitation | 1.14 | 74.7 |
|    | T = 0 | 1.28 | 83.7 |
|    | T = 24 hours | 1.2 | 78.2 |

*Speed was reduced to 150 rpm because at 200 rpm the % torque exceeded 100%

Table 10 summarizes the viscosity results. First, it was found that between pre-agitation/filtration to T=0 there was a decrease in viscosity for formulations F1, F2, and F4-F12 that appeared to be associated with the filtration step, with the exception of F3, F13 and F14, the latter two formulations have the highest [HPMC]. In contrast, for formulations F15 to F18 and F20 to F22, between pre-agitation/filtration to T=0 there was a slight increase in viscosity, consistent with the result for formulation 3 (0.01% w/v 4000 cP HPMC formulation). The only exception to this was F19.

Second, it was found that between T=0 and T=24 hours there was an increase in viscosity that is likely associated with aggregation/formation of particulates, with the exception of F14, F16, F20, and F22. It was noted that for formulations F1 to F7, F1 had the smallest increase in viscosity from T=0 to T=24 hours (1.14 cP to 1.23 cP), F4 had the greatest increase in viscosity from T=0 to T=24 hours (0.64 cP to 1.36 cP), and that the average pre-agitation/filtration sample viscosity=1.24 cP. It was further noted that for formulations F8 to F14, F8 had the greatest increase in viscosity from T=0 to T=24 hours (0.52 cP to 1.29 cP), the average pre-agitation/filtration sample viscosity=1.02 cP—lower, as expected, than the average for F1-F7 (1.24 cP), which contain a higher viscosity grade HPMC. It was further noted that from formulations F15 to F22, F15 had the greatest increase in viscosity from T=0 to T=24 hours (1.32 to 1.55 cP). The relatively high concentration of carbetocin in F15 compared to the other formulations in this group led to more aggregation occurring in F15, hence the higher final viscosity result.

TABLE 11

Assay results pre-agitation/filtration and T = 24 hours, corrected for potency, Formulations 1-22

| | Pre Agitation/Filtration | | T = 24 hours | |
|---|---|---|---|---|
| Time point Experiment | [Carbetocin] (mg/mL) | Rec./theory[1] (%) | [Carbetocin] (mg/mL) | Rec./T = 0[2] (%) |
| 1 | 33.80 | 98.53 | 33.20 | 98.23 |
| 2 | 33.45 | 97.52 | 34.83 | 104.12 |
| 3 | 33.18 | 96.74 | 33.84 | 101.98 |
| 4 | 32.05 | 93.45 | 33.33 | 103.97 |
| 5 | 31.73 | 92.49 | 32.00 | 100.85 |
| 6 | 32.96 | 96.08 | 33.19 | 100.70 |
| 7 | 33.32 | 97.15 | 33.37 | 100.15 |
| 8 | 26.10 | 76.10 | 26.24 | 100.53 |
| 9 | 33.35 | 97.24 | 33.77 | 101.25 |
| 10 | 32.90 | 95.92 | 33.09 | 100.58 |
| 11 | 34.15 | 99.55 | 33.67 | 98.60 |
| 12 | 34.72 | 101.24 | 34.86 | 100.38 |
| 13 | 34.51 | 100.60 | 34.20 | 99.13 |
| 14 | 34.50 | 100.57 | 35.07 | 101.65 |
| 15 | 34.62 | 100.93 | 34.26 | 98.96 |
| 16 | 19.74 | 98.70 | 19.26 | 97.56 |
| 17 | 11.18 | 98.09 | 11.04 | 98.68 |
| 18 | 8.03 | 100.39 | 7.88 | 98.08 |
| 19 | 4.20 | 105.11 | 4.28 | 101.85 |
| 20 | 2.90 | 96.51 | 2.91 | 100.50 |
| 21 | 1.90 | 94.87 | 1.86 | 97.97 |
| 22 | 0.94 | 93.59 | 0.91 | 97.48 |

[1]As a percentage of theoretical carbetocin concentrations (refer to Table 5)
[2]As percentage of initial Pre-Agitation/Filtration result As can be seen from Table 11, re-agitation/filtration assay results were generally good, as was the recovery for the T=24 hours samples. F8 assay was low, in concordance with osmolality and pH results, confirming an error was made when preparing this formulation—its results should be discarded.

TABLE 12

Actual assay results for pre-agitation/filtration and T = 24 hours, Formulations 1-22

| | Pre-agitation/Filtration | | T = 24 hours | |
|---|---|---|---|---|
| Time point Experiment | [Carbetocin] (mg/mL) | Rec./theory[1] (%) | (Carbetocin) (mg/mL) | Rec./T = 0[2] (%) |
| 1 | 32.378 | 94.40 | 31.805 | 98.23 |
| 2 | 32.044 | 93.42 | 33.365 | 104.12 |
| 3 | 31.788 | 92.68 | 32.417 | 101.98 |
| 4 | 30.709 | 89.53 | 31.929 | 103.97 |
| 5 | 30.394 | 88.61 | 30.653 | 100.85 |
| 6 | 31.574 | 92.05 | 31.798 | 100.71 |
| 7 | 31.924 | 93.07 | 31.972 | 100.15 |
| 8 | 25.007 | 72.91 | 25.138 | 100.52 |
| 9 | 31.954 | 93.16 | 32.353 | 101.25 |
| 10 | 31.519 | 91.89 | 31.702 | 100.58 |
| 11 | 32.713 | 95.37 | 32.256 | 98.60 |

TABLE 12-continued

Actual assay results for pre-agitation/filtration and T = 24 hours, Formulations 1-22

| Time point Experiment | Pre-agitation/Filtration [Carbetocin] (mg/mL) | Rec./theory[1] (%) | T = 24 hours (Carbetocin) (mg/mL) | Rec./T = 0[2] (%) |
|---|---|---|---|---|
| 12 | 33.267 | 96.99 | 33.393 | 100.38 |
| 13 | 33.058 | 96.38 | 32.769 | 99.13 |
| 14 | 33.049 | 96.35 | 33.595 | 101.65 |
| 15 | 33.165 | 96.69 | 32.819 | 98.96 |
| 16 | 18.911 | 94.56 | 18.451 | 97.57 |
| 17 | 10.713 | 93.97 | 10.572 | 98.68 |
| 18 | 7.694 | 96.18 | 7.5470 | 98.09 |
| 19 | 4.028 | 100.70 | 4.102 | 101.84 |
| 20 | 2.774 | 92.47 | 2.788 | 100.50 |
| 21 | 1.818 | 90.90 | 1.781 | 97.96 |
| 22 | 0.897 | 89.70 | 0.874 | 97.44 |

[1]As a percentage of theoretical carbetocin concentrations (refer to table 5)
[2]As percentage of initial pre-agitation/filtration result

TABLE 13

Appearance T = 0 and T = 24 hours

| Formulation/ Time point | Appearance T = 0 | T = 24 hours |
|---|---|---|
| 1 | clear solution, free from visible particulates | Large snowflake like clump |
| 2 | clear solution, free from visible particulates | No visible aggregate present |
| 3 | clear solution, free from visible particulates | Several small clumps |
| 4 | clear solution, free from visible particulates | Clumps present, less than in #3 |
| 5 | clear solution, free from visible particulates | Layer of clumps at meniscus forming raft |
| 6 | clear solution, free from visible particulates | Complete raft at meniscus |
| 7 | clear solution, free from visible particulates | Complete raft at meniscus |
| 8 | clear solution, free from visible particulates | One or two specs |
| 9 | clear solution, free from visible particulates | No visible aggregate present |
| 10 | clear solution, free from visible particulates | Several small specs |
| 11 | clear solution, free from visible particulates | No visible aggregate present |
| 12 | clear solution, free from visible particulates | Very few small specs |
| 13 | clear solution, free from visible particulates | Several small flakes |
| 14 | clear solution, free from visible particulates | Similar to 13, slightly less flakes |
| 15 | clear solution, free from visible particulates | Large flakes and gel on glass |
| 16 | clear solution, free from visible particulates | Webby aggregate at meniscus |
| 17 | clear solution, free from visible particulates | Very few small number of particulates |
| 18 | clear solution, free from visible particulates | Very few small number of particulates |
| 19 | clear solution, free from visible particulates | No visible aggregate present |
| 20 | clear solution, free from visible particulates | No visible aggregate present |
| 21 | clear solution, free from visible particulates | No visible aggregate present |
| 22 | clear solution, free from visible particulates | No visible aggregate present |

TABLE 14

MFI data, Formulations 1-22

| Formulation | Time-point (hrs) | ≥1.00-<2.00 μm | ≥2.00-<10.00 μm | ≥10.00-<25.00 μm | ≥25.00 μm |
|---|---|---|---|---|---|
| 1 | F1 T = 0 | 2141 | 495 | 31 | 17 |
|   | F1 T = 24 hrs | 15543 | 8883 | 1784 | 555 |
| 2 | F2 T = 0 | 800 | 222 | 4 | 7 |
|   | F2 T = 24 hrs | 8850 | 2826 | 69 | 14 |
| 3 | F3 T = 0 | 941 | 381 | 28 | 14 |
|   | F3 T = 24 hrs | 7118 | 4768 | 626 | 211 |
| 4 | F4 T = 0 | 898 | 209 | 14 | 2 |
|   | F4 T = 24 hrs | 16013 | 9837 | 918 | 124 |
| 5 | F5 T = 0 | 1011 | 339 | 13 | 21 |
|   | F5 T = 24 hrs | 7273 | 3927 | 529 | 151 |
| 6 | F6 T = 0 | 958 | 407 | 16 | 12 |
|   | F6 T = 24 hrs | 4116 | 1522 | 235 | 38 |
| 7 | F7 T = 0 | 827 | 179 | 12 | 9 |
|   | F7 T = 24 hrs | 3558 | 1664 | 301 | 112 |
| 8 | F8 T = 0 | 508 | 150 | 14 | 6 |
|   | F8 T = 24 hrs | 24127 | 32944 | 8743 | 1172 |
| 9 | F9 T = 0 | 2560 | 581 | 17 | 6 |
|   | F9 T = 24 hrs | 54435 | 13984 | 463 | 152 |
| 10 | F10 T = 0 | 916 | 331 | 18 | 18 |
|   | F10 T = 24 hrs | 21558 | 22707 | 8614 | 2418 |
| 11 | F11 T = 0 | 881 | 258 | 13 | 6 |
|   | F11 T = 24 hrs | 113771 | 23364 | 584 | 123 |
| 12 | F12 T = 0 | 951 | 360 | 27 | 12 |
|   | F12 T = 24 hrs | 170441 | 59900 | 7392 | 1426 |
| 13 | F13 T = 0 | 758 | 151 | 14 | 5 |
|   | F13 T = 24 hrs | 100281 | 103802 | 17830 | 2526 |
| 14 | F14 T = 0 | 493 | 124 | 13 | 7 |
|   | F14 T = 24 hrs | 81309 | 73053 | 13329 | 2257 |

TABLE 14-continued

MFI data, Formulations 1-22

| Formulation | Time-point (hrs) | ≥1.00-<2.00 μm | ≥2.00-<10.00 μm | ≥10.00-<25.00 μm | ≥25.00 μm |
|---|---|---|---|---|---|
| 15 | F15 T = 0 | 1834 | 501 | 37 | 17 |
|  | F15 T = 24 hrs | 7814 | 3514 | 305 | 66 |
| 16 | F16 T = 0 | 1108 | 298 | 5 | 8 |
|  | F16 T = 24 hrs | 4858 | 2037 | 298 | 103 |
| 17 | F17 T = 0 | 1799 | 351 | 11 | 9 |
|  | F17 T = 24 hrs | 4017 | 1058 | 56 | 22 |
| 18 | F18 T = 0 | 1765 | 602 | 18 | 6 |
|  | F18 T = 24 hrs | 6503 | 1835 | 73 | 19 |
| 19 | F19 T = 0 | 746 | 186 | 12 | 6 |
|  | F19 T = 24 hrs | 4241 | 1276 | 52 | 15 |
| 20 | F20 T = 0 | 901 | 251 | 13 | 7 |
|  | F20 T = 24 hrs | 5920 | 1594 | 74 | 37 |
| 21 | F21 T = 0 | 1017 | 264 | 4 | 13 |
|  | F21 T = 24 hrs | 6995 | 2631 | 264 | 85 |
| 22 | F22 T = 0 | 482 | 109 | 5 | 3 |
|  | F22 T = 24 hrs | 9951 | 3504 | 108 | 27 |

Figure 2:
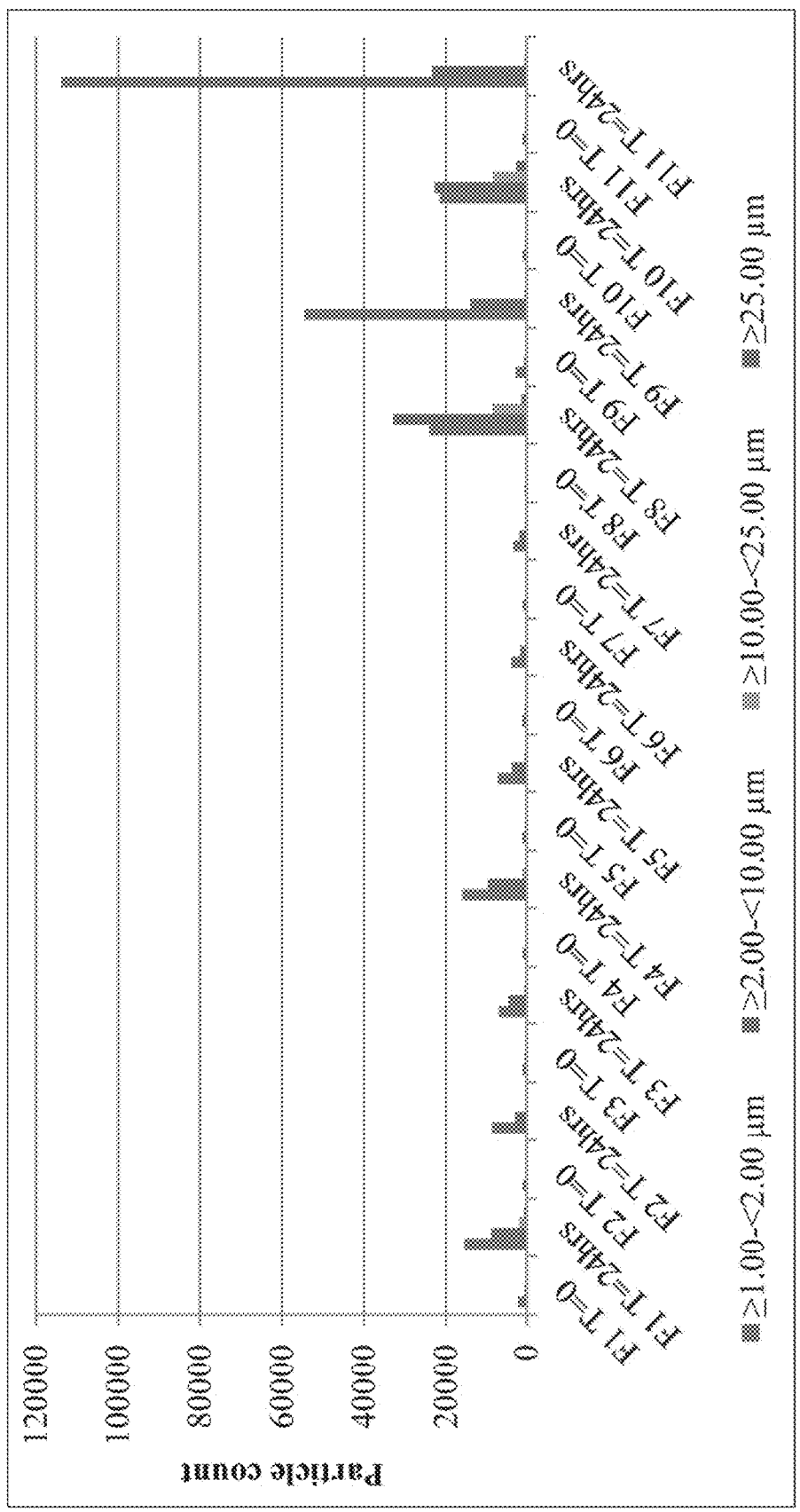
FIG. 2. shows a graph comparing T=0 and T=24 hours particle count for Formulations 1-11.
Figure 3:
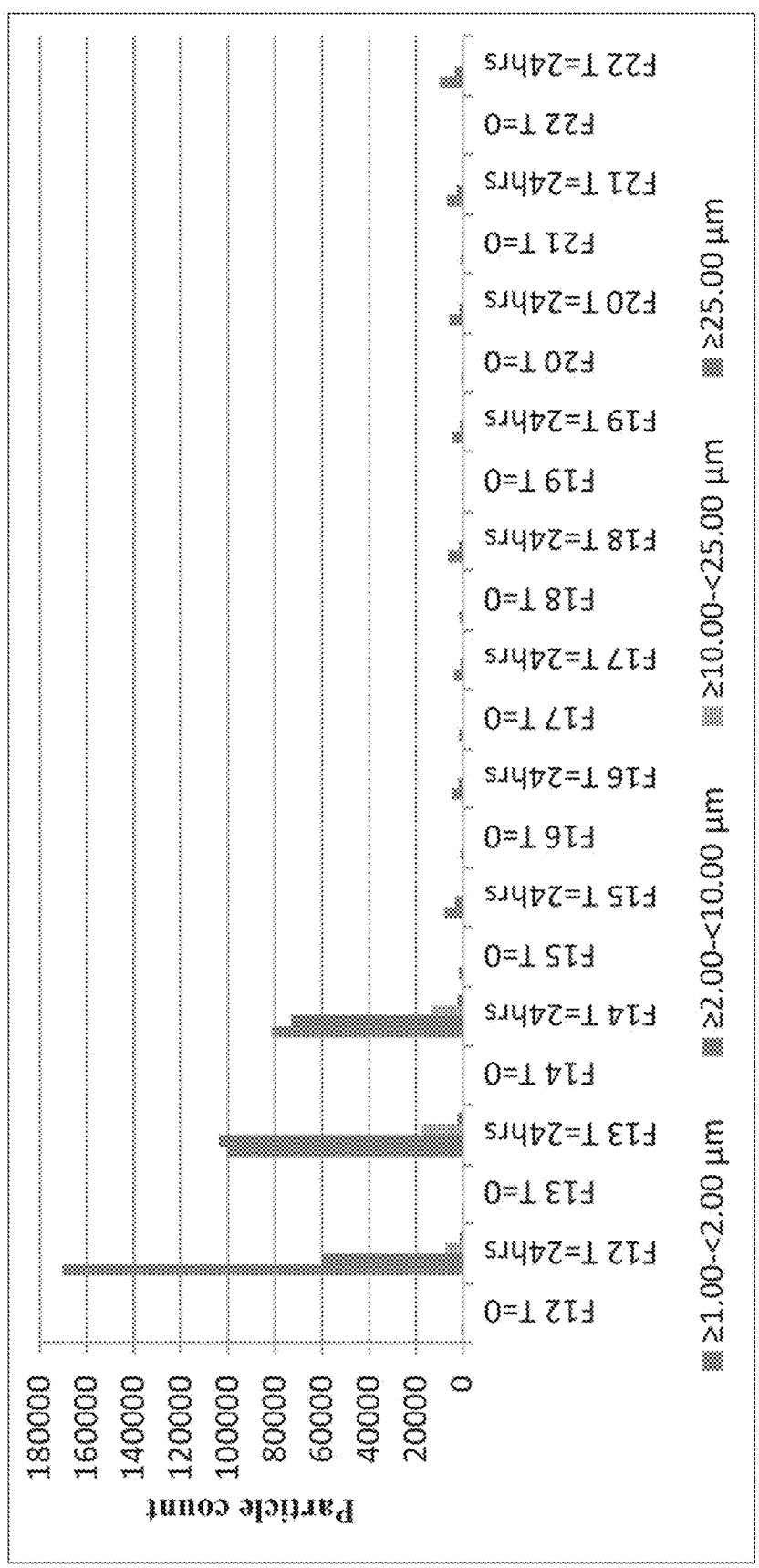
FIG. 3. shows a graph comparing T=0 and T=24 hours particle count for Formulations 12-22.
Figure 4:
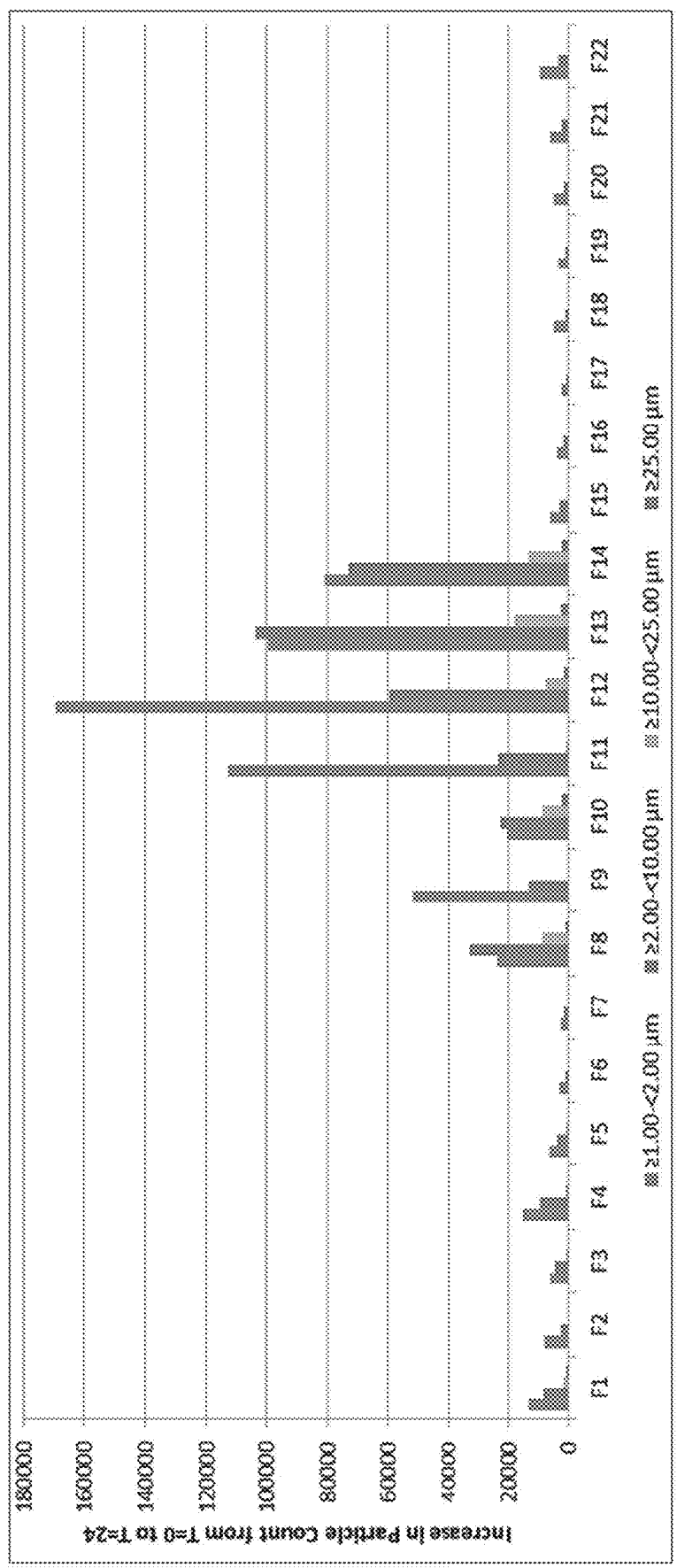
FIG. 4. shows a graph comparing T=0 and T=24 hours particle count for Formulations 1-22.

It was found that at T=24 hours, F2 had the lowest particle count for particles over 10 μm of all formulations at 34.3 mg/mL carbetocin (see Table 14 and FIGS. 2-4). The samples F8-F12 (the formulations containing low viscosity grade HPMC), had higher particle counts for particles over 10 μm at T=24 hours when compared to formulations containing high viscosity grade HPMC (see FIGS. 2 and 3). For example, at T=24 hours, F10 had 11032 particles ≥10 μm, whereas F3 had 837 particles ≥10 μm (both formulations at 34.3 mg/mL carbetocin and 0.01% w/v HPMC) (see FIGS. 2 and 4). F4 was an outlier, the particle counts are higher than what may be expected if following a trend. The high particle count however was in correlation with it also being the formulation which saw the largest increase in viscosity from T=0 to T=24 hours. F16-F22 had low particle counts for large particle sizes (≥10 μm) (see FIGS. 3 and 4). This was anticipated as aggregation is reduced with the decreasing carbetocin concentration.

Figure 5:
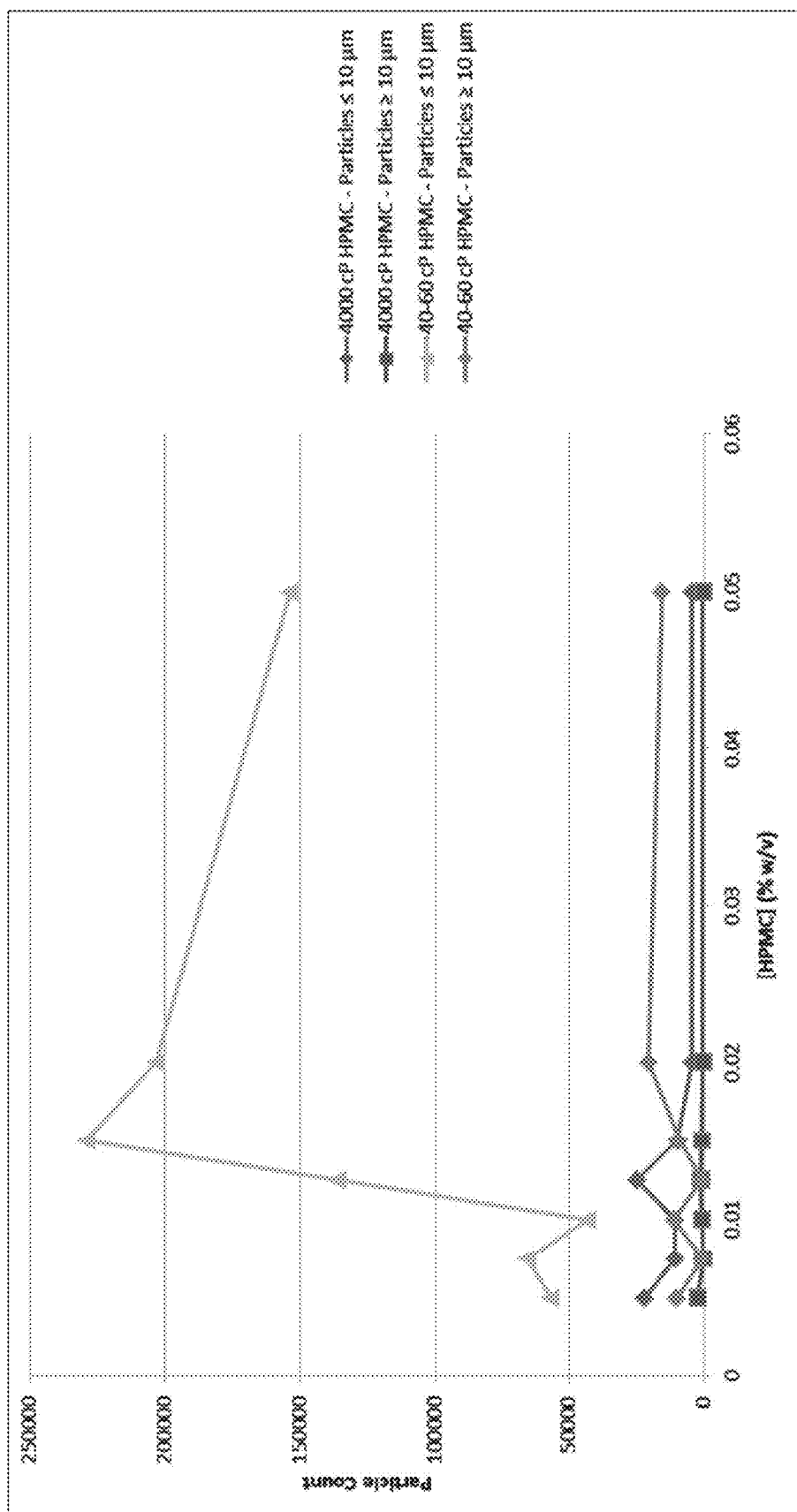
FIG. 5. shows a graph displaying the relationship between HPMC grade/concentration and particle size/count comparing T=0 and T=24 hours particle count for Formulations 1-22.

It was observed that the low viscosity grade HPMC appeared to form a high number of small particles (≥10 μm), including when the HPMC concentration was increased above 0.01% w/v (see FIG. 5). There was also an increase in the number of large particles (≥10 μm) from concentrations of 0.02% w/v for 40-60 cP HPMC (FIG. 5).

Figure 6:
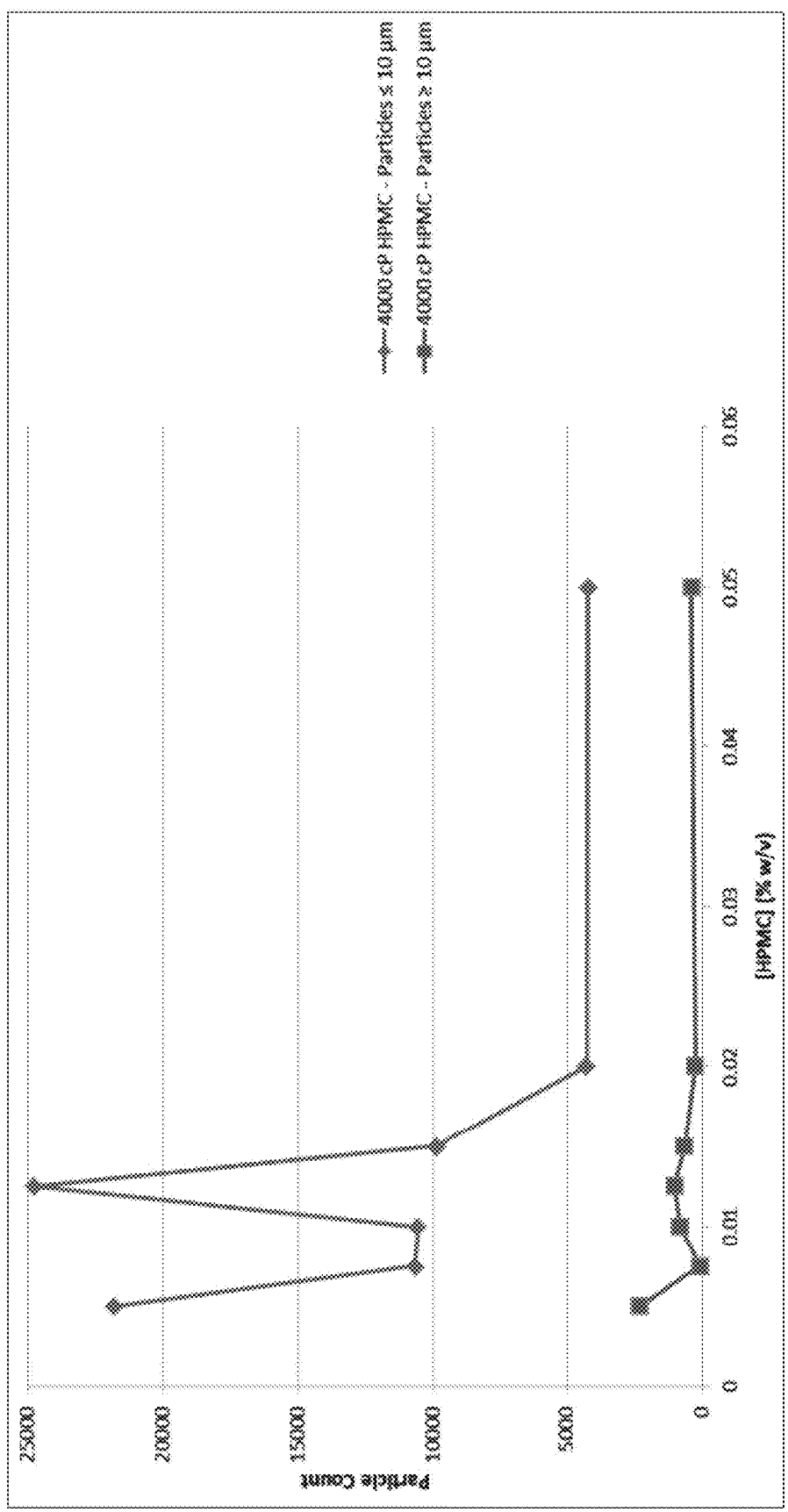
FIG. 6. shows a graph displaying the relationship between 4000 cP HPMC concentration and particle size/count.

It was further observed that large particle count decreased to a minimum at HPMC concentration 0.0075% w/v for 4000 cP HPMC (see FIG. 6). After 0.0075% w/v, the large particle count increased slightly with increasing concentration before peaking at 0.0125% w/v (FIG. 6). Higher concentrations than 0.0125% w/v HPMC brought the particle count back down again—however, it was noted that although results for small and large particles appear low at HPMC concentrations of 0.02 and 0.05% w/v (F6, F7), the visual appearance notes indicated that a raft of aggregate material had formed at the meniscus in the vial, thus leading to low results when the MFI sample was removed from the center of the solution in the vial.

Figure 7:
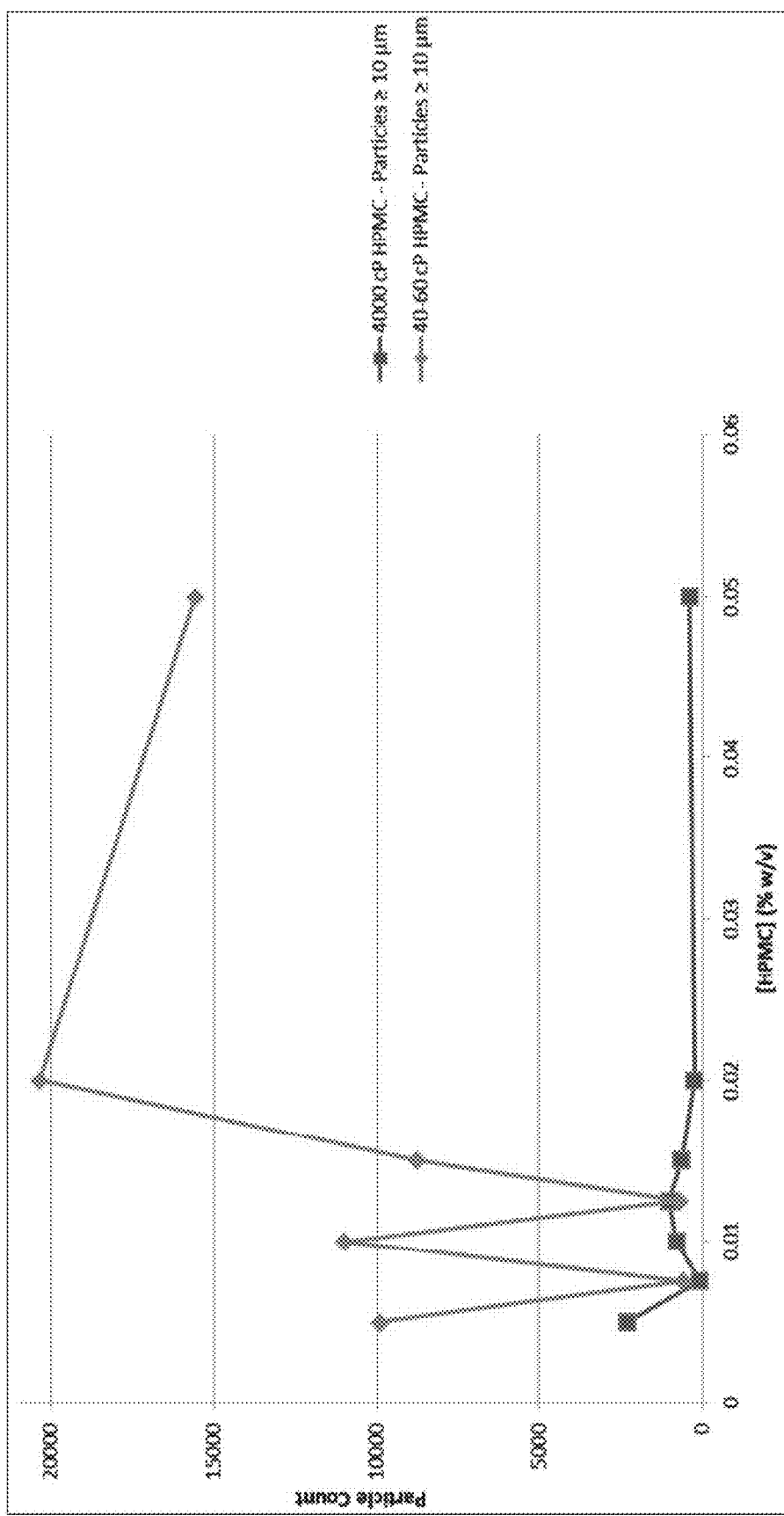
FIG. 7. shows a graph displaying the relationship between HPMC grade/concentration and particle count for particles ≥10 μm.
Figure 8:
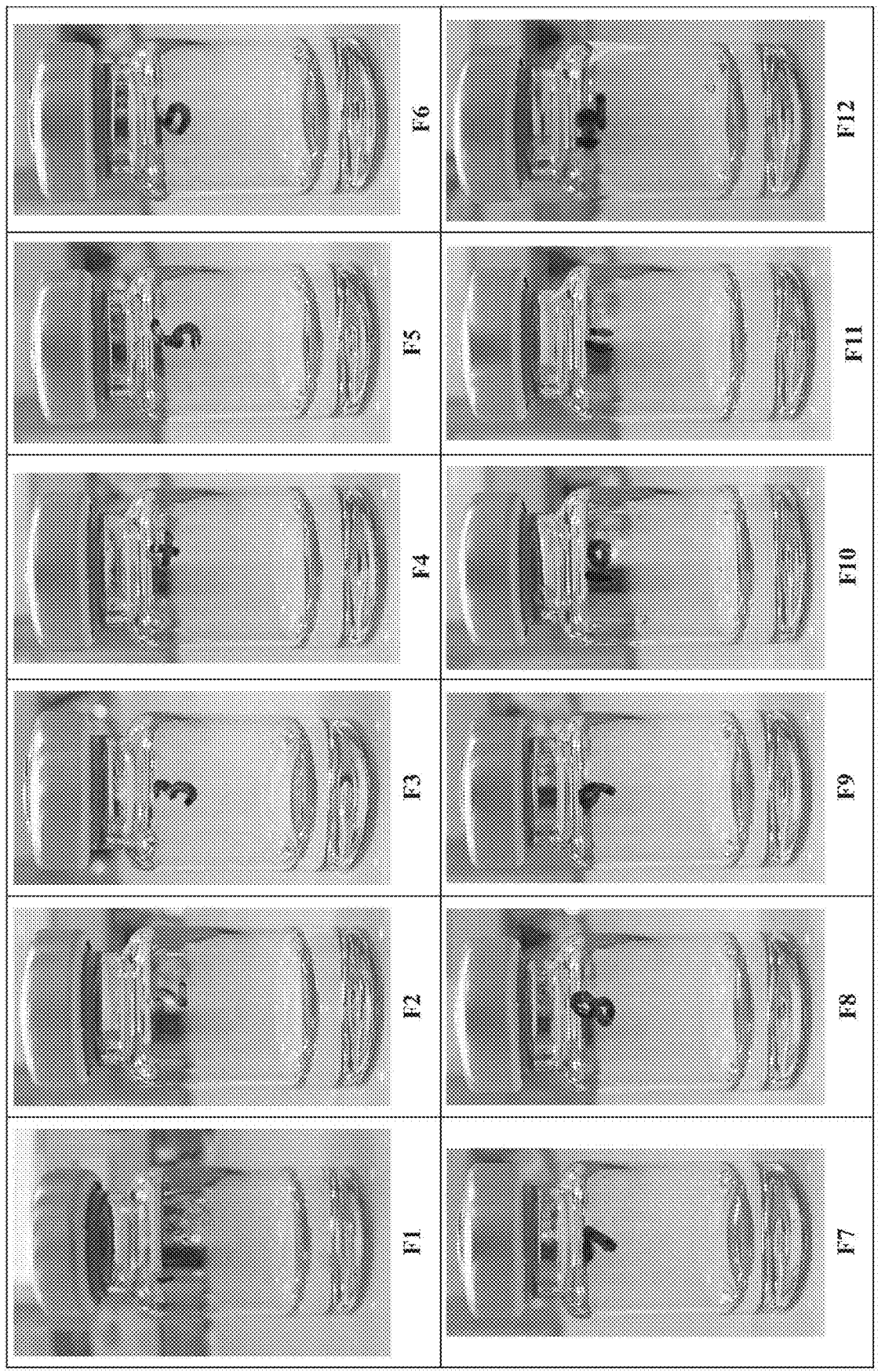
FIG. 8. shows an example image of the appearance of samples F1, F2, F3, F4, F5, F6, F7, F8, F9, F10, F11, and F12 after 24 hours of "post-agitation/filtration $T_{24}$" on the rocker.
Figure 9:
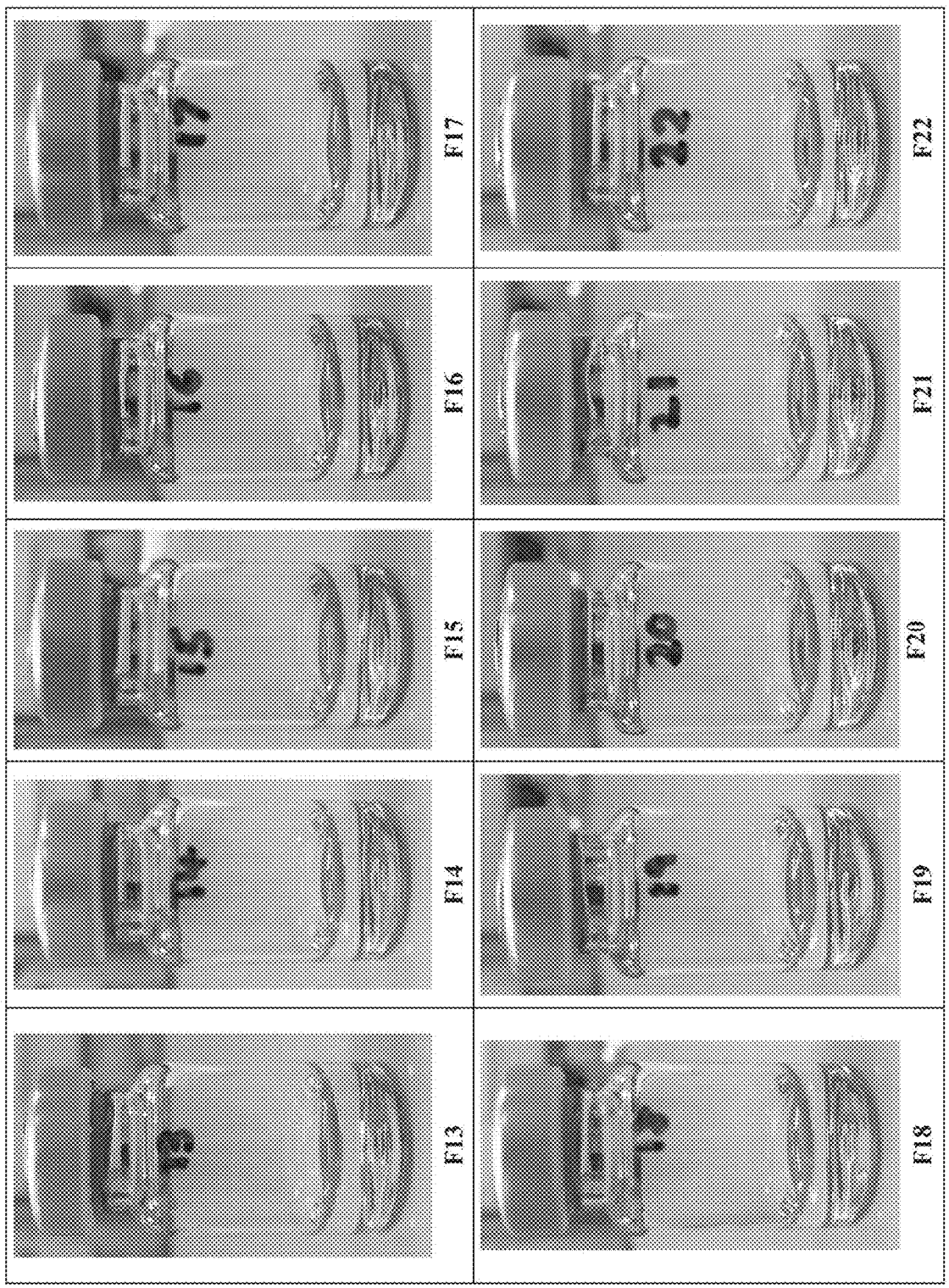
FIG. 9. shows an example image of the appearance of samples F13, F14, F15, F16, F17, F18, F19, F20, F21, and F22 after 24 hours of "post-agitation/filtration $T_{24}$" on the rocker.

Furthermore, the data showed that formulations containing high viscosity grade HPMC generally form fewer large particles than those containing the low viscosity grade HPMC (see FIG. 7). The ratio of HPMC to carbetocin appeared to be important and was more sensitive with 40-60 cP HPMC than it was with 4000 cP HPMC. This suggested that high viscosity grade HPMC was better than low viscosity grade HPMC at inhibiting aggregation. However, the visual appearance must also be taken into account. The photographs (see FIGS. 8, 9, and 10) and notes taken during visual inspection at T=24 hours indicated that F6 and F7 (see FIGS. 8 and 10) contained the most visible aggregates, as they formed a complete raft of aggregate material at the meniscus of the solution. However, this meant that the aggregates were not evenly dispersed throughout the solution, and as a result a low particle count was detected by MFI as the sample was taken from the center of the solution in the vial. The concentration of HPMC appears to be critical; HPMC concentration around 0.0075%-0.01% w/v looks the most positive (see FIG. 7). It should be noted that there is likely a ratio of HPMC to carbetocin, and when the HPMC concentration is increased above this ratio, aggregation (in both visible appearance and MFI particle count) is accelerated.

Figure 11:
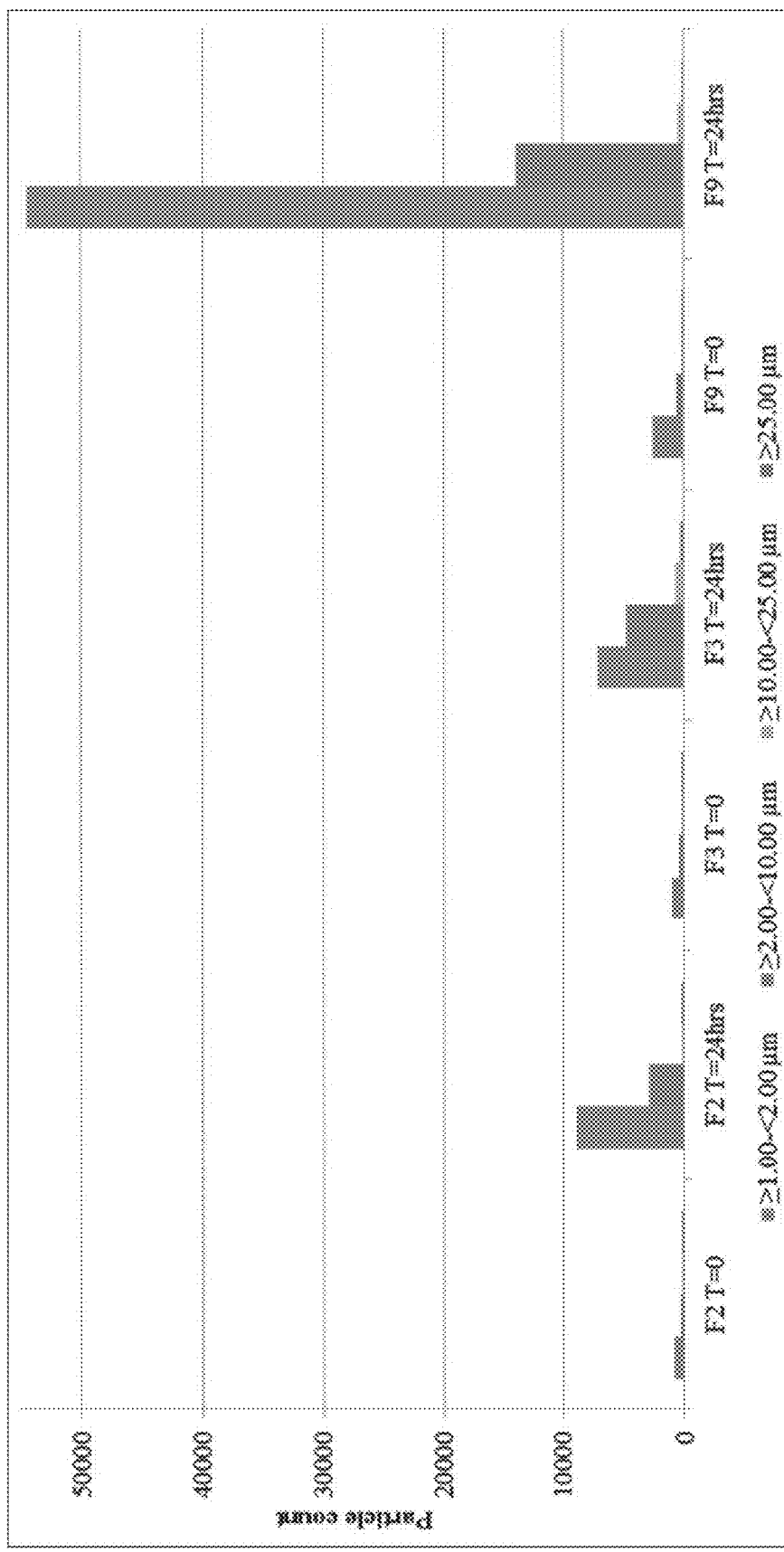
FIG. 11. shows a graph comparing T=0 and T=24 hours particle count for Formulations 2, 3 and 9.

Table 15 below summarizes the MFI data for formulations 2, 3 and 9 and FIG. 11 compares T=0 and T=24 hours particle for formulations 2, 3 and 9.

TABLE 15

MFI data, Formulations 2, 3 and 9.

| Formulation | Time-point (hrs) | ≥1.00-<200 μm | ≥2.00-<10.00 μm | ≥10.00-<25.00 μm | ≥25.00 μm |
|---|---|---|---|---|---|
| 2 | F2 T = 0 | 800 | 222 | 4 | 7 |
|  | F2 T = 24 hrs | 8850 | 2826 | 69 | 14 |
| 3 | F3 T = 0 | 941 | 381 | 28 | 14 |
|  | F3 T = 24 hrs | 7118 | 4768 | 626 | 211 |
| 9 | F9 T = 0 | 2560 | 581 | 17 | 6 |
|  | F9 T = 24 hrs | 54435 | 13984 | 463 | 152 |

Figure 10:
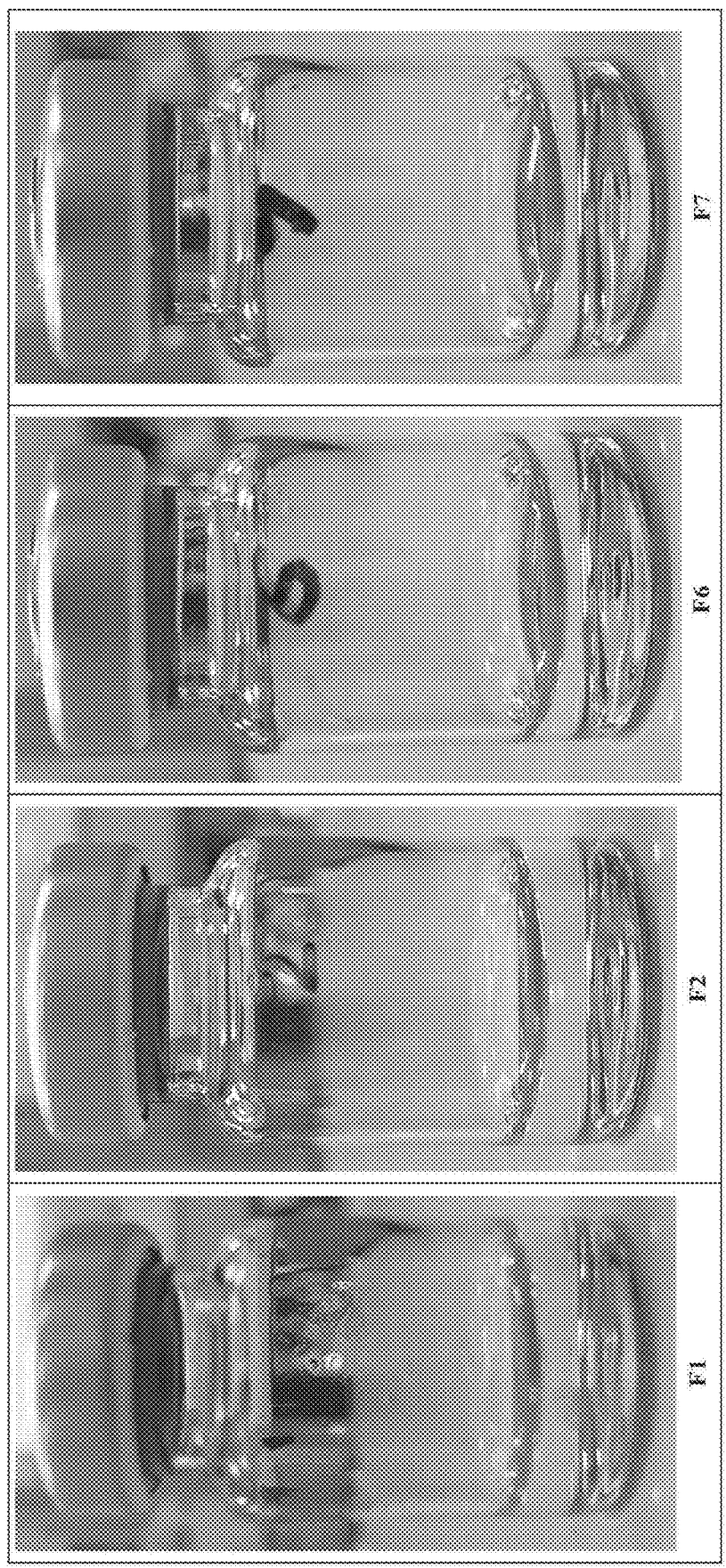
FIG. 10. shows an example image of the appearance of samples F1, F2, F6, and F7 after 24 hours of "post-agitation/filtration $T_{24}$" on the rocker.

As can be seen from Table 15, F2 had the lowest result for particles ≥10 μm across all formulations at 34.3 mg/mL carbetocin. This suggested that the slightly lower concentration of HPMC (0.0075% w/v for F2 versus 0.01% w/v for F3) reduced the rate of aggregation. When this is considered in parallel with the visual appearance of the solutions, a more complete picture is produced. F2 and F9 were both noted as having "no visible aggregate present" at T=24 hours, whereas F3 was noted to have "several small clumps" present. It is also worth noting that although F9 had a significantly higher number of small particles (≥10 μm) at T=24 hours, there were a similar number of particles over 10 μm present in F3 and F9 at T=24 hours. This is likely to mean that at time-points extended beyond 24 hours, F9 would give higher particle count results for particles ≥10 μm as the great number of smaller particles aggregate. Across the suite of analysis, formulation 2 was superior to the other formulations as it had at least the following desired properties:

(a) no visible aggregates in the visual assessment, including via photographs (see FIG. 10);
(b) the lowest particle count for particles over 10 μm for 34.3 mg/mL carbetocin formulations in MF;
(c) meets pH specification for pre filter/agitation at all time points; and
(d) viscosity result below average for 34.3 mg/mL carbetocin formulations at T=24 (1.23 cP, avg=1.31 cP).

What is claimed is:

1. A method for preparing a carbetocin drug product comprising carbetocin or a pharmaceutically acceptable salt thereof with increased resistance to aggregation, wherein the concentration of carbetocin is about 1 mg/mL to about 70 mg/mL, comprising:
    (a) dissolving carbetocin or a pharmaceutically acceptable salt thereof and one or more excipients chosen from a surface active agent, solubilizer, tonicity enhancer, an agent to adjust the pH, and combinations thereof to form an aqueous solution;
    (b) agitating the aqueous solution from step (a) for a time period of hours to form aggregate-forming solids;
    (c) removing the formed aggregate-forming solids from the agitated solution to form a post-agitation solution; and
    (d) adding the post-agitation solution to a container to form a final drug product: wherein the carbetocin drug product has increased resistance to aggregation when tested with shaking stress compared to an aqueous solution of carbetocin that has not been treated according to steps (b) and (c).

2. The method of claim 1, wherein the carbetocin drug product is substantially free of the aggregate-forming solids.

3. The method of claim 1, wherein the aqueous solution comprising carbetocin comprises a surface active agent, which is a visco-elastic polymer that is a cellulose derivative selected from the group consisting of hydroxypropyl cellulose (HPC), hydroxypropyl methylcellulose (HPMC), and carboxy methyl ethyl cellulose (CMEC).

4. The method of claim 1, wherein the solubilizer is a hydrotrope, amino acid, or cyclodextrin selected from the group consisting of sodium benzoate, sodium salicylate, sodium benzene sulfonate, sodium benzene disulfonate, sodium cinnamate, sodium 3-hydroxy-2-naphthoate, sodium para-toluene sulfonate, sodium cumene sulfonate, nicotinamide, N,N-diethylnicotinamide, N,N-dimethyl benzamide, para-aminobenzoic acid hydrochloride, procaine hydrochloride, caffeine, sodium alkanoate, urea, N,N-dimethyl urea, arginine, methyl-R-cyclodextrin, randomly methylated-β-cyclodextrin (RM-β-CD), sulfobutylether-β-cyclodextrin (SBE-β-CD), epichlorohydrin-β-cyclodextrin, and carboxy methyl epichlorohydrin beta cyclodextrin.

5. The method of claim 4, wherein the hydrotrope is present in a concentration ranging from about 50 mM to about 500 mM.

6. The method of claim 3, wherein the cellulose derivative is present in an amount ranging from 0.0075% to 0.05% w/v.

7. The method of claim 1, wherein the excipient is chosen from sorbitol, ethylenediaminetetraacetic acid (EDTA), potassium sorbate, acetate, and combinations thereof.

8. The method of claim 1, wherein the carbetocin is present in a concentration of about 10 mg/mL to about 40 mg/mL.

9. The method of claim 1, wherein the carbetocin is present in a concentration of about 25 mg/mL to about 35 mg/mL.

* * * * *